（12） United States Patent
Gungor et al.

(10) Patent No.: US 7,381,730 B2
(45) Date of Patent: Jun. 3, 2008

(54) 3-ARYLQUINAZOLINE DERIVATIVES AS SELECTIVE ESTROGEN RECEPTOR BETA MODULATORS

(75) Inventors: Timur Gungor, Pennington, NJ (US); James R. Corte, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 210 days.

(21) Appl. No.: 10/387,666

(22) Filed: Mar. 13, 2003

(65) Prior Publication Data

US 2003/0220227 A1 Nov. 27, 2003

Related U.S. Application Data

(60) Provisional application No. 60/364,561, filed on Mar. 15, 2002.

(51) Int. Cl.
 A61K 31/517 (2006.01)
 C07D 239/88 (2006.01)
 C07D 239/93 (2006.01)

(52) U.S. Cl. ............... 514/266.21; 514/266.31; 544/284; 544/287

(58) Field of Classification Search ........... 514/266.21, 514/266.31, 252.02, 252.01; 544/284, 287, 544/238
 See application file for complete search history.

(56) References Cited

U.S. PATENT DOCUMENTS

| | | | | |
|---|---|---|---|---|
| 3,951,660 | A | * | 4/1976 | Hagemann et al. ......... 430/570 |
| 4,411,890 | A | | 10/1983 | Momany ..................... 514/17 |
| 5,412,093 | A | * | 5/1995 | Jung et al. ................. 540/221 |
| 5,480,883 | A | * | 1/1996 | Spada et al. ............... 514/249 |
| 5,700,822 | A | * | 12/1997 | Hirth et al. ................. 514/380 |
| 5,948,775 | A | * | 9/1999 | Koko et al. ............. 514/217.06 |
| 6,518,277 | B1 | * | 2/2003 | Sadhu et al. ............. 514/266.1 |
| 6,559,160 | B1 | * | 5/2003 | Schall et al. ............... 514/284 |

FOREIGN PATENT DOCUMENTS

| | | |
|---|---|---|
| JP | 10-259176 A * | 9/1998 |
| WO | WO 89/07110 | 8/1989 |
| WO | WO 89/07111 | 8/1989 |
| WO | WO 93/04081 | 3/1993 |

OTHER PUBLICATIONS

Brine, G.A. et al., "Carbon-13 Nuclear Magnetic Resonance Spectra of Methaqualone Metabolites", J. Het. Chem., Jan. 1979, vol. 16, No. 1, pp. 25-28.*
Bundgaard, H., "Design and Application of Prodrugs", A Textbook of Drug Design and Development, Harwood Academic Publishers, Krogsgaard-Larsen, P. et al., eds., pp. 113-191 (1991).
Bundgaard, H., ed., Design of Prodrugs, Elsevier Science Publishers B.V. (1985) (table of contents).

Cava, M.P. et al., "Thionation Reactions of Lawesson's Reagents", Tetrahedron, vol. 41, No. 22, pp. 5061-5087 (1985).
Coppola, G.M., "The Chemistry of 4H-3, 1-Benzoxazin-4-ones", J. Heterocyclic Chem., vol. 36, pp. 563-588 (1999).
Coppola, G.M., "The Chemistry of Isatoic Anhydride", Synthesis, vol. 7, pp. 505-536 (1980).
Edwards, J.P. et al., "Nonsteroidal Androgen Receptor Agonists Based on 4-(trifluoromethyl)-2H-pyrano[3,2-g]quinolin-2-one", Bioorganic & Medicinal Chemistry Letters, vol. 9, pp. 1003-1008.
Greene, T.W. et al., eds., Protective Group in Organic Synthesis, Third Edition, John Wiley & Sons, Inc. (1999) (table of contents).
Hamann, L.G. et al., "Discovery of a Potent, Orally Active, Nonsteroidal Androgen Receptor Agonist: 4-Ethyl-1,2,3,4-tetrahydro-6-(trifluoromethyl)-8-pyridono[5,6-g]-quinoline (LG121071)", J. Med. Chem., vol. 42, pp. 210-212 (1999).
Kuiper, G.G.J.M. et al., "Interaction of Estrogenic Chemicals and Phytoestrogens with Estrogen Receptor β", Endocrinology, vol. 139, No. 10, pp. 4252-4263 (1998).

(Continued)

Primary Examiner—James O. Wilson
Assistant Examiner—Tamthom N. Truong
(74) Attorney, Agent, or Firm—Burton Rodney; Maureen P. O'Brien

(57) ABSTRACT

Novel quinazoline derivatives possessing activity as estrogen receptor beta (ERβ) modulators are provided which have the general formula I

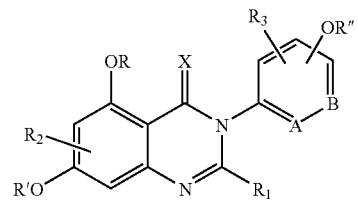

wherein
 X is O or S;
 A and B are each independently CR''' or N;
 R, R' and R'' are each independently hydrogen, alkyl, benzyl, p-methoxybenzyl, allyl, or Si(R$_4$)$_3$, wherein at least one of R, R' and R'' is hydrogen;
 R''' is hydrogen, halogen, CF$_3$, OR$_5$, S(O)$_n$R$_6$, NR$_7$R$_8$, cycloalkyl or alkyl;
 R$_1$, R$_2$ and R$_3$ are each independently hydrogen, halogen, CF$_3$, OR$_5$, S(O)$_n$R$_6$, NR$_7$R$_8$, cycloalkyl or alkyl;
 R$_4$ is a alkyl;
 R$_5$, R$_6$, R$_7$ and R$_8$ in each functional group are each independently hydrogen, cycloalkyl or alkyl; and
 n is an integer from 0 to 2.

In addition, a method is provided for preventing, inhibiting or treating the progression or onset of pathological conditions associated with the estrogen receptor and to pharmaceutical compositions containing such compounds.

18 Claims, No Drawings

OTHER PUBLICATIONS

Martinet, J., "Synthéses dans la série de l' α-naphtindol", Compt. Rend., vol. 166, pp. 851-853 (1918).

Marvel, C.S. et al., "Isatin", Organic Synthesis, Collective vol. 1, Second Edition, John Wiley & Sons, Inc., Gilman, H. et al., eds., pp. 327-330 (1941).

Mezheritskii, V.V. et al., "The Properties of Orthoesters and Their Applications in Organic Synthesis", Russian Chemical Reviews, vol. 42, No. 5, pp. 392-412 (1973) (English translation).

Newman, H. et al., "The Synthesis of the Ring-B Sulfur Analog of Epigriseofulvin", The Journal of Organic Chemistry, vol. 34, No. 11, pp. 3484-3491 (1969).

Schwarz, G., "2,4-dimethylthiazole (Thiazole, 2,4-dimethyl-)", Organic Syntheses, Collective vol. 3, pp. 332-333 (1955).

Wagner, G. et al., "Eine neue Methode zur Darstellung von 1,2,3,4-Tetrahydrochinazolindithionen-(2,4)", Z. Chem., vol. 7, pp. 339-340 (1967).

Wermuth, C.G. et al., "Designing Prodrugs and Bioprecursors I: Carrier Prodrugs", The Practice of Medicinal Chemistry, Academic Press, Wermuth, C.G., ed., pp. 671-696 (1996).

* cited by examiner

3-ARYLQUINAZOLINE DERIVATIVES AS SELECTIVE ESTROGEN RECEPTOR BETA MODULATORS

CROSS-REFERENCE TO RELATED APPLICATIONS

This application claims priority from provisional application Ser. No. 60/364,561, filed Mar. 15, 2002, incorporated herein by reference in its entirety.

FIELD OF THE INVENTION

The present invention relates to novel, substituted quinazoline compounds and their derivatives, methods of using such compounds in the treatment of estrogen receptor-associated conditions, such as bone disorders, for example osteoporosis, and to pharmaceutical compositions containing such compounds.

BACKGROUND OF THE INVENTION

The estrogen hormone has a broad spectrum of effects on tissues in both females and males. Many of these biological effects are positive, including maintenance of bone density, cardiovascular protection, central nervous system (CNS) function and the protection of organ systems from the effects of aging. However, in addition to its positive effects, estrogen also is a potent growth factor in the breast and endometrium that increases the risk of cancer.

Until recently, it was assumed that estrogen binds to a single estrogen receptor (ER) in cells. However, a second estrogen receptor, ER beta (ERβ), has been identified and cloned, with the original ER being renamed ER alpha(ERα). *Endocrinology* 1998 139 4252-4263. ERβ and ERα share about a 50% identity in the ligand-binding domain and only 20% homology in their amino-terminal transactivation domain. The difference in the identity of the two ER subtypes accounts for the fact that small compounds may demonstrate a higher affinity to bind to one subtype over the other.

Further, ERβ and ERα are believed to have varied distributions and functions in different tissues. For example, in rats, ERβ is strongly expressed in brain, bone and vascular epithelium, but weakly expressed in uterus and breast, relative to ERα. Further, ERα knockout mice are sterile and exhibit little or no evidence of hormone responsiveness of reproductive tissues. In contrast, ERβ knockout mice are fertile and exhibit normal development and function of breast and uterine tissue. These observations suggest that selectively targeting ERβ over ERα could confer beneficial effects in several important diseases, such as Alzheimer's disease, anxiety disorders, depressive disorders, osteoporosis and cardiovascular diseases, without the liability of reproductive system side effects. Selective effects on ERβ expressing tissues over uterus and breast could be achieved by agents that selectively interact with ERβ over ERα.

Accordingly, it would be advantageous to develop a series of novel compounds, which selectively modulate ERβ receptors and may be employed to treat a variety of estrogen-dependent pathological conditions.

SUMMARY OF THE INVENTION

In accordance with the present invention, substituted quinazoline derivatives are provided which have the structure of formula I wherein
X is oxygen (O) or sulfur (S);
A and B are each independently CR''' or N;
R, R' and R'' are each independently hydrogen, alkyl, benzyl, p-methoxybenzyl, allyl, or $Si(R_4)_3$, wherein at least one of R, R' and R'' is hydrogen;
R''' is hydrogen, halogen, $CF_3$, $OR_5$, $S(O)_nR_6$, $NR_7R_8$, cycloalkyl or alkyl;
$R_1$, $R_2$ and $R_3$ are each independently hydrogen, halogen, $CF_3$, $OR_5$, $S(O)_nR_6$, $NR_7R_8$, cycloalkyl or alkyl;
$R_4$ is alkyl:
$R_5$, $R_6$, $R_7$ and $R_8$ in each functional group are each independently hydrogen, cycloalkyl or alkyl; and
n is an integer from 0 to 2.

The compounds of formula I above further include all pharmaceutically acceptable salts, stereoisomers and prodrug esters of formula I.

The compounds of formula I modulate the function of the estrogen receptor beta (ERβ) and include compounds which are, for example, selective agonists, partial agonists, antagonists or partial antagonists of the ERβ. Consequently, the compounds of the present invention may be used in the treatment of multiple diseases or disorders associated with ERβ activity, such as the treatment of bone disorders, cardiovascular diseases, hypercholesterolemia, hypertriglyceridemia, vasomotor disorders, urogenital disorders, prostatic hypertrophy, endometrial hyperplasia and cancer. Further, the compounds of the present invention may have central nervous system (CNS) action and therefore may be useful for the treatment of multiple CNS disorders, such as neurodegenerative diseases.

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

In addition, a method is provided for preventing, inhibiting or treating the onset of pathological conditions associated with the estrogen receptor, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting or treating the diseases as defined above and hereinafter, wherein a therapeutically effective amount of a combination of a compound of formula I and another compound of formula I and/or at least one other type of therapeutic agent, is administered to a mammalian, i.e., human patient in need of treatment.

Preferred are compounds of formula I having the structure Ia:

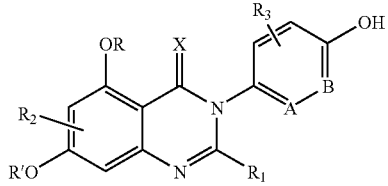

wherein A, B, R', R''', $R_1$, $R_2$, $R_3$, $R_4$, $R_5$, $R_6$, $R_7$, $R_8$ and n are as described above.

Preferred compounds of formula I having structure Ia are those compounds wherein a. R and R' are hydrogen;

b. R and R' are hydrogen; and $R_1$, $R_2$, $R_3$ are hydrogen, and b. R' is hydrogen;

$R_1$ and $R_2$ are hydrogen; and $R_3$ is fluoro, chloro or methyl.

Further embodiments of compounds of the invention include the following:

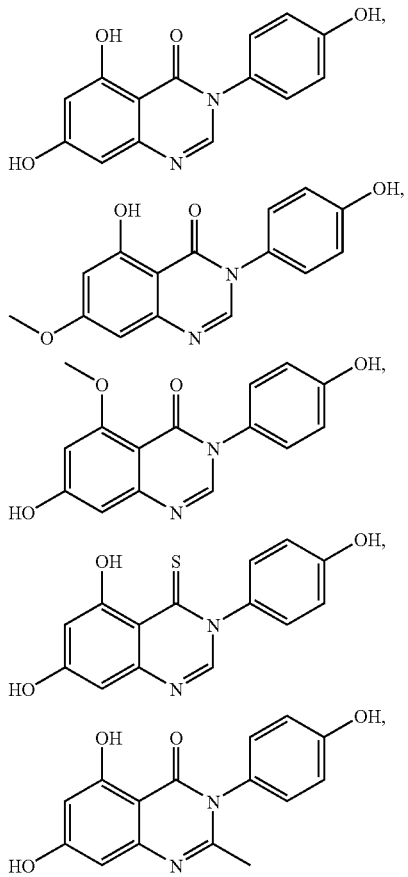

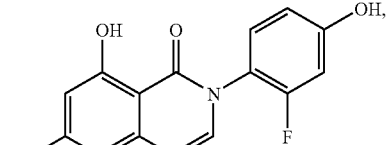

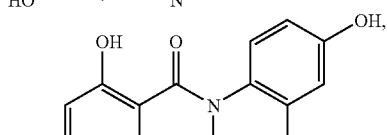

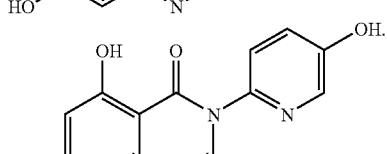

DETAILED DESCRIPTION OF THE INVENTION

The following abbreviations are employed herein:
DMAP=4-(dimethylamino)pyridine
DMF=N,N-dimethylformamide
EtOAc=ethyl acetate
EtSNa=sodium ethylthiolate
ESI=electron spray injection
g=gram(s)
HPLC=high performance liquid chromatography
h or hr=hour(s)
LC/MS=high performance liquid chromatography/mass spectrometry
MeOH=methyl hydroxide
M+H=parent plus a proton
M−H=parent minus a proton
mg=milligram(s)
min=minute(s)
mL=milliliter(s)
mmol=millimole(s)
mol=mole(s)
MP=melting point
MS or Mass Spec=mass spectrometry
NaHMDS=sodium hexamethyldisilazane
NMR=nuclear magnetic resonance
RT=room temperature
THF=tetrahydrofuran
μL=microliter(s)

The following definitions apply to the terms as used throughout this specification, unless otherwise limited in specific instances.

The term "alkyl" or "alk" as employed herein, alone or as part of another group, includes both straight and branched chain hydrocarbons, containing 1 to 20 carbons, preferably 1 to 10 carbons, more preferably 1 to 8 in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. "Substituted alkyl" includes an alkyl group optionally substituted with one or more functional groups which are attached commonly to such chains, such as, but not limited to, halo, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, oxo, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl, alkylthio and the like.

The term "cycloalkyl" means a cycloalkyl group preferably containing 3 to 8 carbon atoms, such as cyclopropyl, cyclobutyl, cyclopentyl, cyclohexyl. Any of such groups may be optionally substituted with one or more substituents, such as, but not limited to any of the substituents described above for substituted alkyl.

As used herein, the term "benzyl" refers to $CH_2C_6H_5$.

The term "allyl" as used herein, refers to a —$CH_2CH=CH_2$.

As used herein, the term "halo" or "halogen" refers to fluorine, chlorine, bromine and iodine.

The term "modulator" refers to a chemical compound with capacity to either enhance (e.g., "agonist" activity) or inhibit (e.g., "antagonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

a.) *The Practice of Medicinal Chemistry,* Camille G. Wermuth et al., Ch 31, (Academic Press, 1996);

b.) *Design of Prodrugs,* edited by H. Bundgaard, (Elsevier, 1985); and c.) *A Textbook of Drug Design and Development,* P. Krogsgaard-Larsson and H. Bundgaard, eds. Ch 5, pgs 113-191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center.

Preferred salts of the compounds of formula I which contain a basic group include monohydrochloride, hydrogensulfate, methanesulfonate, phosphate or nitrate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods, for example, chromatographic or fractional crystallization.

The compounds of the invention may be prepared as shown in the following reaction schemes and description thereof, as well as relevant published literature procedures available to those skilled in the art. Exemplary reagents and procedures for these reactions appear hereinafter and in the working Examples.

Reaction Scheme 1

The reaction of benzoxazinones compounds of formula II

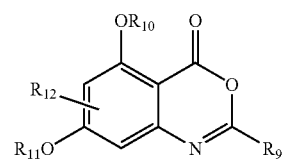

Formula II in which $R_9$ is hydrogen, $CF_3$, cycloalkyl or alkyl;

$R_{10}$ and $R_{11}$ are alkyl, benzyl or p-methoxybenzyl, allyl or $Si(R_4)_3$;

$R_4$ is or alkyl, $R_{12}$ is hydrogen, halogen, $CF_3$, $OR_5$, $S(O)_nR_6$, $NR_7R_8$, cycloalkyl or alkyl;

$R_5$, $R_6$, $R_7$ and $R_8$ for each functional group are independently hydrogen, cycloalkyl or alkyl; and n is an integer from 0 to 2, with the arylamino derivatives of formula III

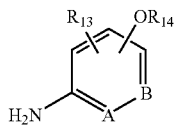

Formula III where
A and B are independently CR''' or N;
$R_{13}$ is hydrogen, halogen, $CF_3$, $OR_5$, $S(O)_nR_6$, $NR_7R_8$, cycloalkyl or alkyl;
$R_5$, $R_6$, $R_7$ and $R_8$ for each functional group are hydrogen, cycloalkyl or alkyl;
R''' is hydrogen, halogen, $CF_3$, $OR_5$, $S(O)_nR_6$, $NR_7R_8$, cycloalkyl or alkyl;
$R_{14}$ is alkyl, benzyl or p-methoxybenzyl, allyl or $Si(R_4)_3$;
$R_4$ is or alkyl; and
n is an integer from 0 to 2,
in excess of the arylamino compound, without any solvent or in stoichiometric quantities of formula II in the presence of an organic solvent such as toluene or xylene at a temperature of between 20° and 180° C., will give the compounds of formula IVa

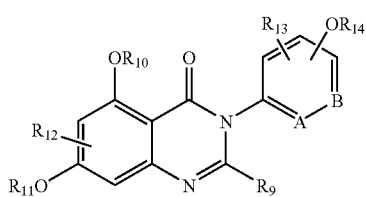

Formula IVa where A, B, $R_9$, $R_{10}$, $R_{11}$, $R_{12}$, $R_{13}$, $R_{14}$, are as defined above.

Compounds of formula I where A, B, $R_2$ and $R_3$ are as defined above, X=O; $R_1$ is hydrogen, $CF_3$, cycloalkyl or alkyl; and at least one of R, R' and R" is hydrogen, are obtained by the selective ether cleavage reactions of compounds of general formula IVa by employing known procedures, depending on the nature of the protecting groups, generally known to those skilled in the art (see, for example, T. W. Greene & P. G. M. Wuts, *Protecting Groups in Organic Synthesis*, 3$^{rd}$ Edition, 1999 [Wiley]).

Compounds of General Formula IVb

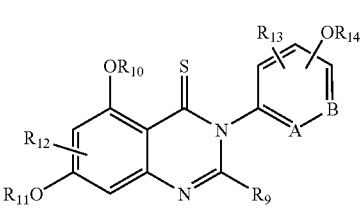

Formula IVb where A, B, $R_9$, $R_{10}$, $R_{11}$, $R_{12}$, $R_{13}$, $R_{14}$, are as defined above, are obtained from the reaction of compounds of general formula IVa with a thiation reagent such as phosphorus pentasulfide ($P_4S_{10}$), or Lawesson's reagent employing procedures generally known to those skilled in the art. (see, for example, *Tetrahedron*, 41, 5061 (1985); *Org. Synth. Coll. Vol.* 3, 332; 1955).

The same ether cleavage methods mentioned above can then be applied to the compounds of general formula IVb to provide the compounds of formula I where A, B, R, R', R", R''', $R_2$ and $R_3$ are as defined above; X=S; $R_1$ is hydrogen, $CF_3$, cycloalkyl or alkyl. Alternatively, the same compounds can be obtained directly by thiation of the compounds of general formula I where A, B, R, R', R", R''', $R_2$ and $R_3$ are as defined above; X=O; and $R_1$ is hydrogen, $CF_3$, cycloalkyl or alkyl, via one of the thiation methods mentioned above.

Reaction Scheme 1

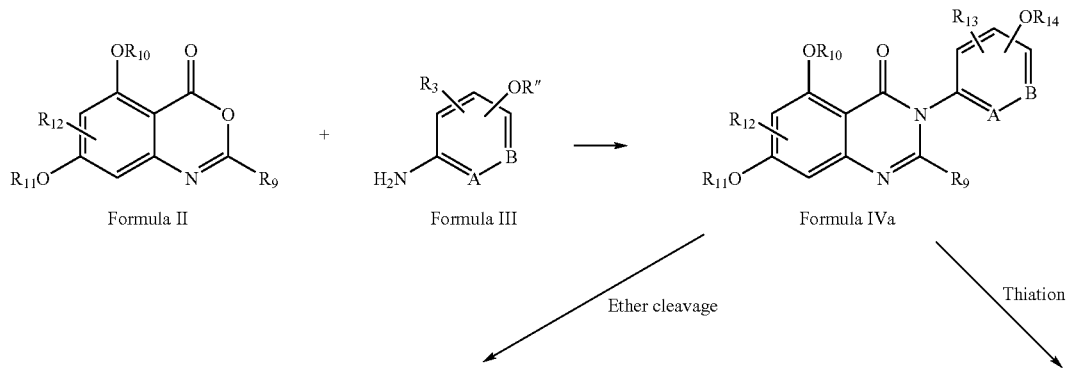

-continued

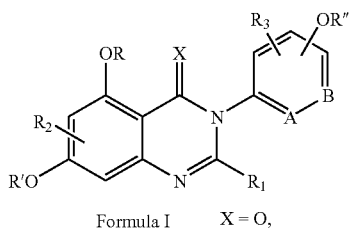
Formula I  X = O,

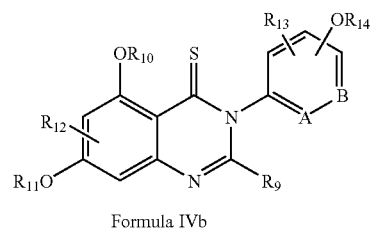
Formula IVb

Thiation

Ether cleavage

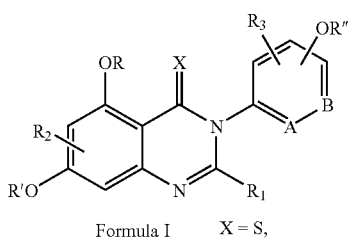
Formula I  X = S,

The benzoxazinones compounds of formula II

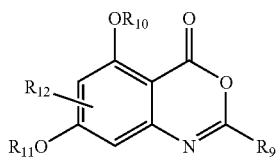
Formula II where $R_9$, $R_{10}$, $R_{11}$ and $R_{12}$ are as defined above, can be obtained by the reaction of anthranilic acid derivatives of general formula V

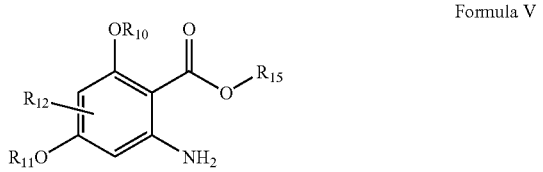
Formula V where $R_{10}$, $R_{11}$ and $R_{12}$ are as defined above and $R_{15}$ is H or a alkyl, with orthoesters of general formula VI

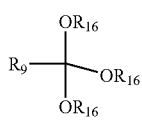
Formula VI where $R_9$ is as defined above and $R_{16}$ is hydrogen or alkyl. Alternatively, methods such as those described in *J. Heterocyclic Chemistry* 36, 563, (1999), could be utilized to obtain compounds of formula II. The orthoesters of general formula VI are either commercially available or may be prepared according to methods generally known to those skilled in the art. (See, for example, the General Review on *Properties of Orthoesters and their Use in Organic Synthesis*, Mezheritskii, V. V.; Olekhnovich, E. P.; Dorofeenko, G. N. Nauchno-Issled. *Inst. Fiz. Org. Khim., Rostov-on-Don, USSR Usp. Khim.* (1973), 42(5), 896-940). Anthranilic acid derivatives of general formula V are either commercially available or may be prepared according to methods generally known to those skilled in the art. One convenient route to prepare compounds of formula V is shown in reaction scheme 1.1 below.

The commercially available aminoanisoles of general formula VII (or their acid salts)

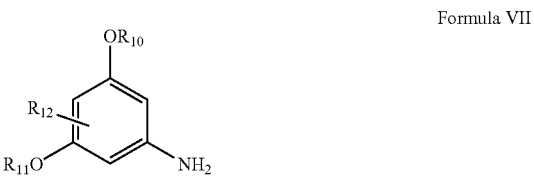
Formula VII where $R_{10}$, $R_{11}$, $R_{12}$ are as defined above, are reacted with oxalylchloride according to the known literature procedures (*Organic Synthesis Col. Vol. I* p. 327.; Martinet *J. Compt Rend* 1918; 166:851; *J. Org. Chem*, 1969, 34 (11) 3484-91) to yield the 1H-indole-2,3-diones of general formula VIII where $R_{10}$, $R_{11}$, $R_{12}$ are as defined above.

Reaction Scheme 1.1

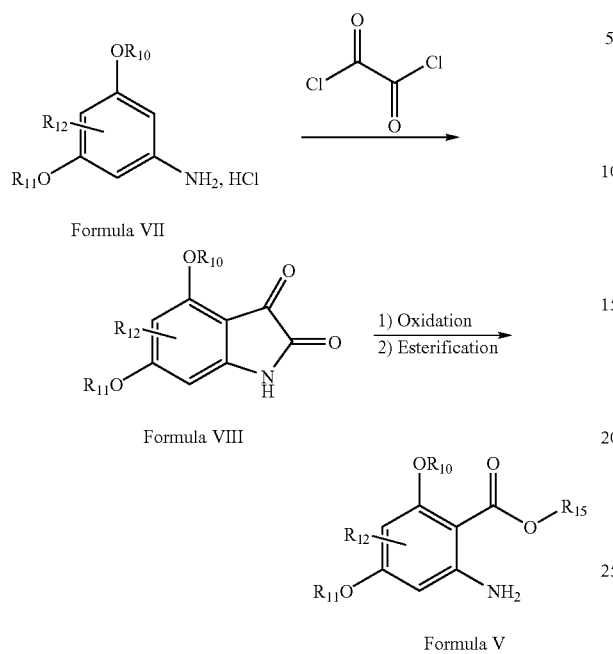

Formula VII

Formula VIII

Formula V

Reaction Scheme 2a

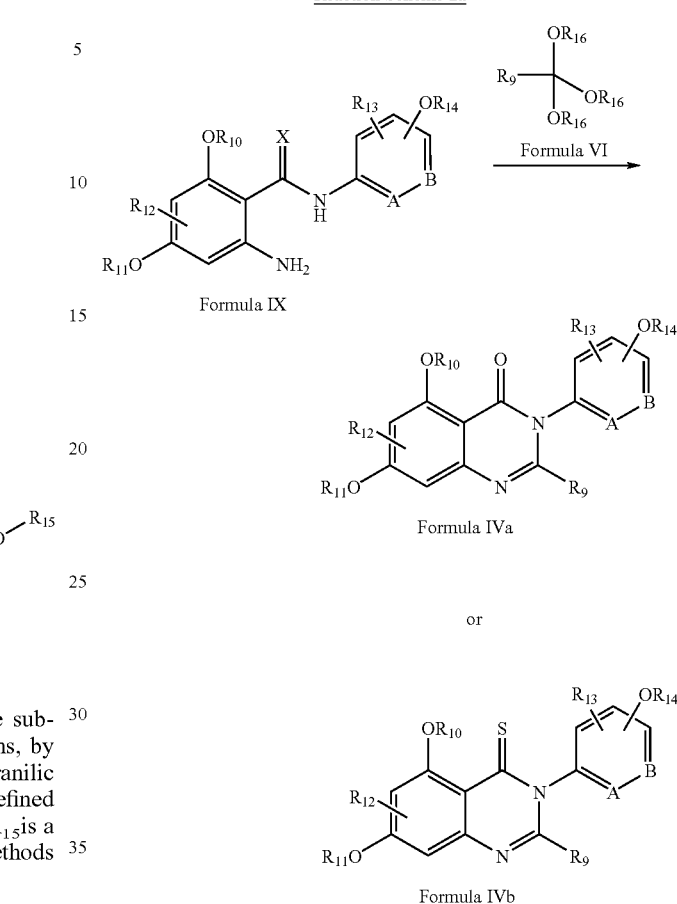

Formula IX

Formula IVa or

Formula IVb

The isatines of general formula VIII may then be subjected to an oxidation reaction, under basic conditions, by using $H_2O_2$/NaOH to yield the corresponding anthranilic acid of general formula V, where $R_{10}$, $R_{11}$, $R_{12}$ are as defined above and $R_{15}$ is H. Compounds of formula V were $R_{15}$ is a alkyl can be obtained by the classical esterification methods as known in the literature.

Reaction Scheme 2a and 2b

The reaction of compounds of general formula IX

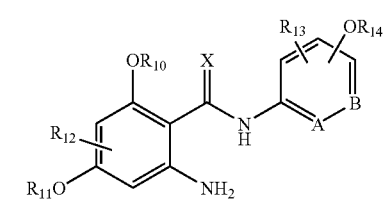

Formula IX where A, B, X, $R_{10}$, $R_{11}$, $R_{12}$, $R_{13}$, and $R_{14}$ are as defined above, with the appropriate reagent selected from the compounds of general formula VI

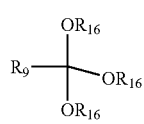

Formula VI where $R_9$ and $R_{16}$ are as defined above, without any solvent, or in the presence of an organic solvent at a temperature between 20° C. and 150° C., will provide, according to Scheme 2a, the compounds of general formula IVa or IVb where A, B, $R_9$, $R_{10}$, $R_{11}$, $R_{12}$, $R_{13}$, $R_{14}$, are as defined above.

Compounds of Formula IVa and IVb can be converted to the compounds of formula I where $R_1$ is hydrogen, $CF_3$, cycloalkyl or alkyl, as described previously in reaction scheme 1.

Alternatively the reaction of compounds of general formula IX

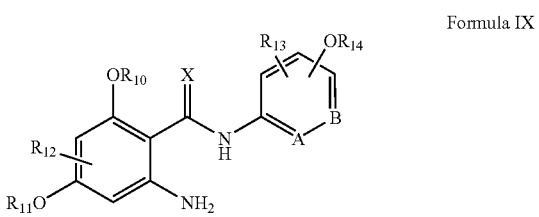

Formula IX where A, B, X, $R_{10}$, $R_{11}$, $R_{12}$, $R_{13}$, and $R_{14}$ are as defined above, with the appropriate reagent selected from the compounds of general formula X

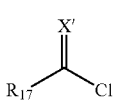

Formula X where X' is O or S; $R_{17}$ is hydrogen, halogen, $CF_3$, $OR_5$, $S(O)_nR_6$, $NR_7R_8$, cycloalkyl or alkyl; $R_5$, $R_6$, $R_7$ and $R_8$ for each functional group are each independently hydrogen, cycloalkyl or a alkyl; and n is an integer from 0 to 2; without any solvent, or in the presence of an organic solvent at a temperature between 20° C. and 150° C., will give the compounds of general formula XI where A, B, X, $R_{10}$, $R_{11}$, $R_{12}$, $R_{13}$, and $R_{14}$ are as defined above; $R_{18}$ is hydrogen, $CF_3$, $OR_5$, $S(O)_nR_6$, $NR_7R_8$, cycloalkyl or alkyl; $R_5$, $R_6$, $R_7$ and $R_8$ for each functional group are each independently hydrogen, cycloalkyl or alkyl; and n is an integer from 0 to 2.

Reaction Scheme 2b

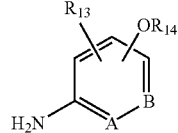

Formula X

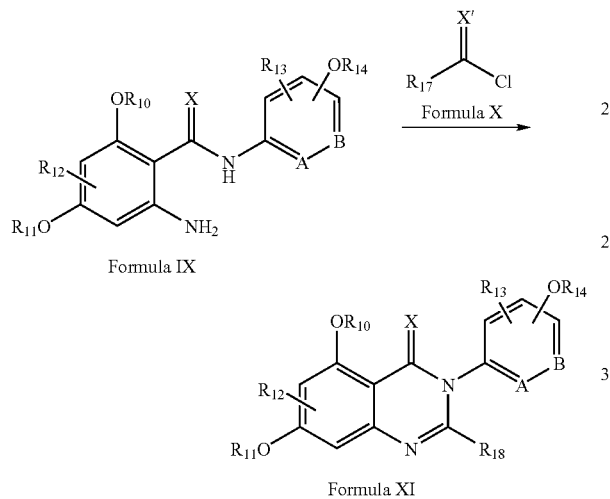

One can obtain compounds of general formula I where A, B, X, R, R', R", R'", $R_2$ and $R_3$ are as defined above; $R_1$ is hydrogen, $CF_3$, $OR_5$, $S(O)_nR_6$, $NR_7R_8$, cycloalkyl or alkyl; $R_5$, $R_6$, $R_7$ and $R_8$ for each functional group are each independently hydrogen, cycloalkyl or a alkyl; and n is an integer from 0 to 2, by the selective ether cleavage reactions of compounds of formula XI through various procedures generally known in the art, depending on the nature of the protecting groups, as previously described herein.

Compounds of general formula I where A, B, X, R, R', R", R'", $R_2$ and $R_3$ are as defined above and $R_1$ is a halogen, can be provided from compounds of general formula XI, where $R_{18}$ is a halogen precursor, e.g., OH or $NH_2$, via various halogenation methods known in the literature. Halogenation is performed prior to the ether cleavage reaction described above.

One can obtain compounds of general formula IX where A, B, $R_{10}$, $R_{11}$, $R_{12}$ $R_{13}$, $R_{14}$ are as defined above and X is O or S by the reaction of isatoic anhydrides of general formula XII Formula XII

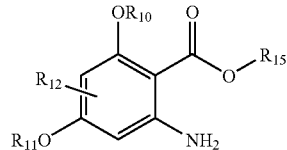

where $R_{10}$, $R_{11}$, $R_{12}$ are as defined above and X' is O or S, with arylamines of formula III Formula III

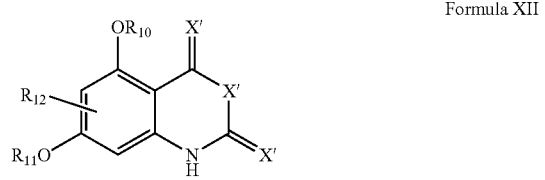

where A, B, $R_{13}$, $R_{14}$ are as defined above, in an organic solvent, such as ethanol in the presence of an organic base, (e.g., dimethylaminopyridine), at a temperature between 0° C. and 190° C., according to Scheme 2.1 below.

Reaction Scheme 2.1

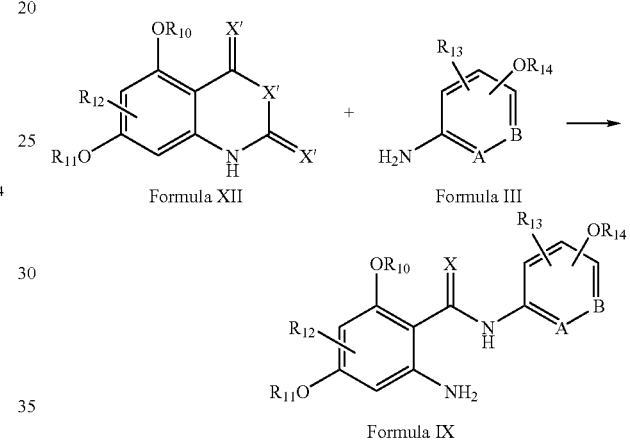

Alternatively, compounds of general formula IX where A, B, $R_{10}$, $R_{11}$, $R_{12}$ $R_{13}$, $R_{14}$ are as defined above and X is S can be obtained from the corresponding compounds where X is O by the reaction of a thiation reagent, such as phosphorus pentasulfide ($P_4S_{10}$), or Lawesson's reagent, according to procedures generally known to those skilled in the art and as previously described herein.

Compounds of general formula XII where $R_{10}$, $R_{11}$, $R_{12}$ are as defined above and X' is O or S, may be prepared according to procedures described in the literature. For example, see Coppola, M., *The Chemistry of Isatoic Anhydride Synthesis* (1980), Vol. 7, 505-36; Wagner, G., Roth, L., Z. Chem. (1967) 7 339.

Reaction Scheme 3

The reaction of anthranilic acid derivatives of general formula V

Formula V

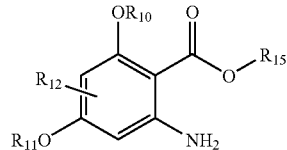

where $R_{10}$, $R_{11}$, $R_{12}$ are as defined above and $R_{15}$ is hydrogen or a alkyl group with an iso (thio) cyanate compound of general formula XIII

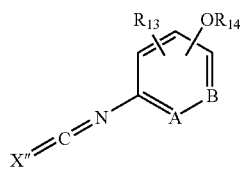

Formula XIII where $R_{13}$, $R_{14}$ are as defined above and X" is O or S, without any solvent or in an organic solvent, such as toluene, at a temperature between 20° C. and 260° C., will give the compounds of general formula XIV

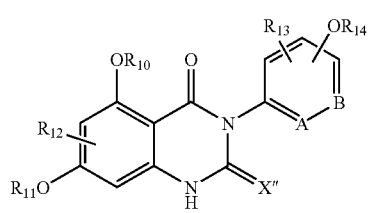

Formula XIV where A, B, $R_{10}$, $R_{11}$, $R_{12}$, $R_{13}$, $R_{14}$ are as defined above and X" is O or S.

Compounds of general formula XIV can be easily transformed to compounds of formula I by the classical reactions of organic chemistry known to one skilled in the art, including alkylation, oxidation, reduction, halogenation, nucleophilic substitution, diazonium salt formation and halogenation reactions according to the reaction Scheme 3 below.

For example, chlorination of the compounds of general formula XIV where A, B, $R_{10}$, $R_{11}$, $R_{12}$, $R_{13}$, $R_{14}$, are as defined above and X" is O, using reagents like $SOCl_2$ or $POCl_3$ will provide the corresponding compounds of general formula XV.

These compounds can either be dehalogenated by hydrogenation or substituted by appropriate nucleophiles followed by an oxidation reaction to yield compounds of general formula XVI where A, B, $R_{10}$, $R_{11}$, $R_{12}$, $R_{13}$ and $R_{14}$ are as defined above; $R_{18}$ is hydrogen, $OR_5$, $S(O)_nR_6$, $NR_7R_8$, cycloalkyl or alkyl; $R_5$, $R_6$, $R_7$ and $R_8$ for each functional group are each independently hydrogen, cycloalkyl or a alkyl; n is an integer from 0 to 2.

Reaction Scheme 3

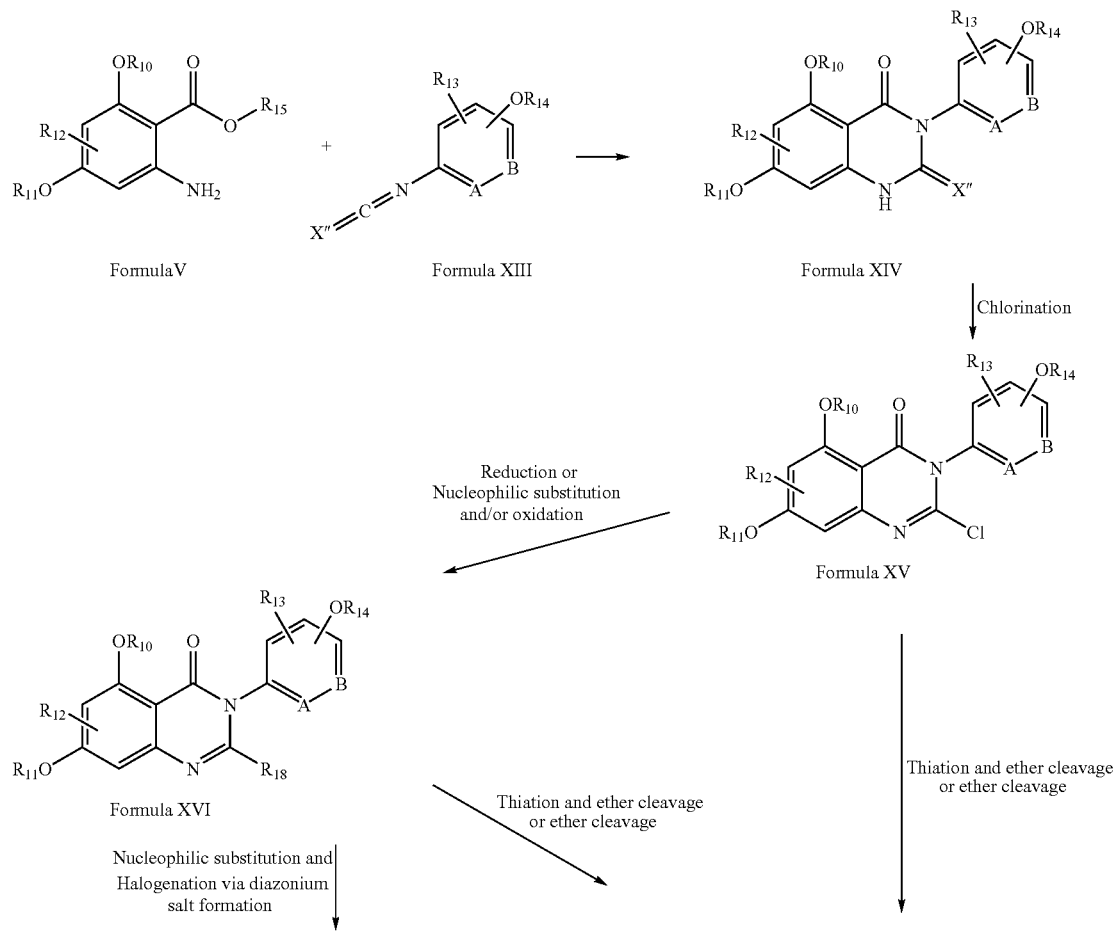

-continued

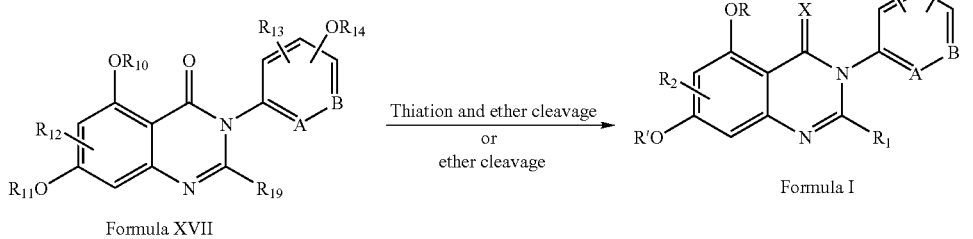

Formula XVII → Formula I

Thiation and ether cleavage or ether cleavage

Compounds of formula XVI where $R_{18}$ is $NH_2$ can be further functionalized by, for example, diazo salt formation and subsequent treatment by different reagents according to known procedures in the literature to yield compounds of general formula XVII where A, B, $R_{10}$, $R_{11}$, $R_{12}$, $R_{13}$, $R_{14}$, are as defined above; $R_{19}$ is hydrogen, halogen, $OR_5$, $S(O)_n R_6$, $NR_7R_8$, cycloalkyl or alkyl; $R_5$, $R_6$, $R_7$ and $R_8$ for each functional group are each independently hydrogen, cycloalkyl or a alkyl, n is an integer from 0 to 2.

Thiation followed by the ether cleavage or ether cleavage reaction of the compounds of general formula XVII will provide the compounds of formula I wherein
X is O or S;
A and B each independently are CR''' or N;
$R_5$, $R_6$, $R_7$ and $R_8$ for each functional group are each independently hydrogen, cycloalkyl or a alkyl; and
n is an integer from 0 to 2.

Alternatively, in accordance with reaction scheme 4, one can obtain the compounds of general formula XVIII where A, B, $R_{10}$, $R_{11}$, $R_{12}$, $R_{13}$, $R_{14}$, are as defined above; and $R_{20}$ is $OR_5$, $S(O)_n R_6$, $NR_7R_8$, cycloalkyl or alkyl; $R_5$, $R_6$, $R_7$ and $R_8$ are each independently hydrogen, cycloalkyl or a alkyl; and n is an integer from 0 to 2, from the compounds of general formula XIV, where A, B, $R_{10}$, $R_{11}$, $R_{12}$, $R_{13}$, $R_{14}$ and X'' are as defined above, by alkylation of formula XIV, followed by a nucleophilic displacement reaction, followed by oxidation. Subsequent thiation and ether cleavage will provide the corresponding compounds of formula I.

Reaction Scheme 4

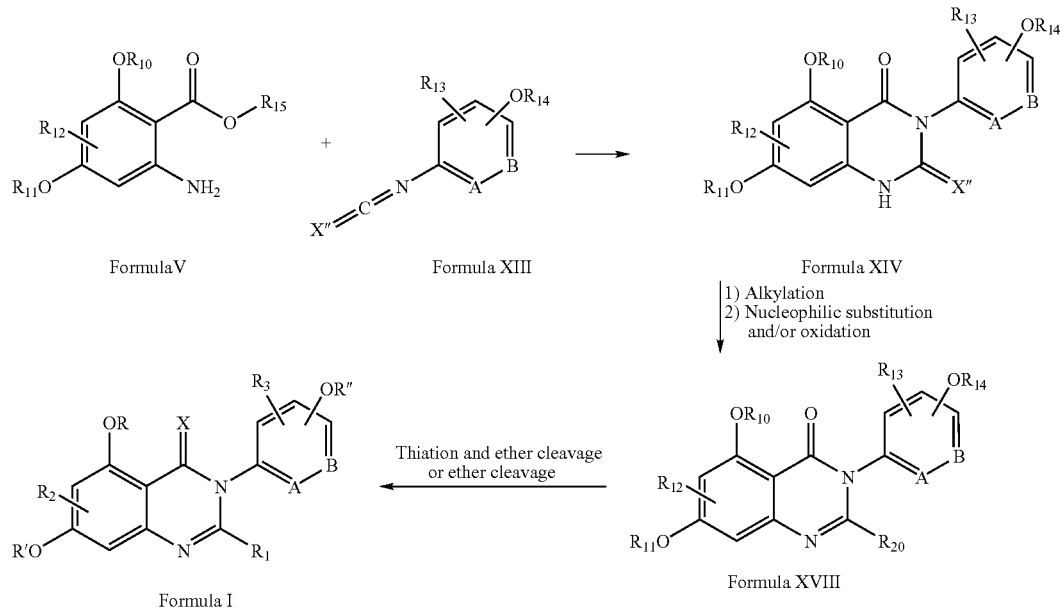

$R_1$, $R_2$ and $R_3$ are each independently are hydrogen, halogen, $CF_3$, $OR_5$, $S(O)_n R_6$, $NR_7R_8$, cycloalkyl or alkyl;
R, R' and R'' are each independently hydrogen, alkyl, benzyl, p-methoxybenzyl, an allyl or $Si(R_4)_3$,
R''' is hydrogen, halogen, $CF_3$, $OR_5$, $S(O)_n R_6$, $NR_7R_8$, cycloalkyl or alkyl;
$R_4$ is a alkyl One may obtain addition salts, particularly pharmaceutically acceptable addition salts, from the compounds of formula I. For example, the compounds of formula I may contain an acidic free phenol or thiol group, such as the salts of sodium, potassium and calcium. Alternatively, the compounds of formula I may contain an amino group, such as an inorganic or organic acid, for example, hydrochloride, methanesulfonate, acetate, maleate, succinate, fumarate, sulfate, lactate or citrate.

Utility & Combinations

A. Utilities

The compounds of the present invention modulate the function of the estrogen receptor beta (ERβ), and include compounds which are, for example, selective agonists, partial agonists, antagonists or partial antagonists of the ERβ. Thus, the present compounds are useful in the treatment of a condition or disorder which can be treated by modulating the function or activity of an ERβ in a subject, wherein treatment comprises prevention, partial alleviation or cure of the condition or disorder. Modulation may occur locally, for example, within certain tissues of the subject, or more extensively throughout a subject being treated for such a condition or disorder.

Accordingly, the compounds of the present invention can be administered to mammals, preferably humans, for the treatment of a variety of conditions and disorders, including, but not limited to bone disorders, e.g., osteoporosis (including glucocorticoid-induced osteoporosis), osteopenia, Paget's disease and peridontal disease; cardiovascular diseases (including fibroproliferative conditions); hypercholesterolemia; hypertriglyceridemia; vasomotor disorders (e.g., hot flashes); urogenital disorders (e.g., urinary incontinence); prostatic hypertrophy; endometrial hyperplasia; and cancer, including prostate cancer, uterine cancer, ovarian cancer, breast cancer and endometrial cancer. Further, the compounds of the present invention may have central nervous system action and therefore may be useful for the treatment of multiple CNS disorders, such as neurodegenerative diseases (e.g., improvement of cognitive function and the treatment of dementia, including Alzheimer's disease and short-term memory loss).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s) or other pharmaceutically active materials.

For example, the compounds of the present invention may be employed in combination with other modulators of the estrogen receptor beta and/or with other suitable therapeutic agents useful in the treatment of the aforementioned disorders, such as, but not limited to, anti-osteoporosis agents, cholesterol lowering agents, growth promoting agents, modulators of bone resorption and cardiovascular agents.

Examples of suitable anti-osteoporosis agents for use in combination with the compounds of the present invention include bisphosphonates (e.g., alendronate, risedronate, ibandronate and zolendrate), parathyroid hormone, PTH fragments and PTH analogues (e.g. PTH-(1-84) and PTH-(1-34)) and calcitonins.

Examples of suitable cholesterol lowering agents for use in combination with the compounds of the present invention include HMG-CoA reductase inhibitors (e.g., pravastatin, lovastatin, atorvastatin, simvastatin, NK-104 (a.k.a. itavastatin, nisvastatin or nisbastatin) and ZD-4522 (a.k.a. rosuvastatin, atavastatin or visastatin)), MTP inhibitors, fibrates (e.g., gemfibrozil) and bile acid sequestrants.

Examples of suitable growth promoting agents for use in combination with the compounds of the present invention include growth hormone secretagogues, such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin $5\text{-}HT_D$ agonists, such as sumatriptan, or agents which inhibit somatostatin or its release, such as physostigmine and pyridostigmine.

Examples of suitable modulators of bone resorption for use in combination with the compounds of the present invention include estrogen; selective estrogen receptor modulators (e.g., tamoxifen, lasofoxifene, TSE-424 and raloxifene); selective androgen receptor modulators, such as those disclosed in Edwards, *Bio. Med. Chem. Let.,* 1999 9, 1003-1008 and *J. Med. Chem.,* 1999 42, 210-212; hormone replacement therapies; vitamin D and analogues thereof (e.g., 1,25-dihydroxy vitamin D3); elemental calcium and calcium supplements; cathepsin K inhibitors; chloride channel inhibitors (e.g., ClC-7 inhibitors); MMP inhibitors; vitronectin receptor antagonists; Src $SH_2$ antagonists; Src kinase inhibitors; vacular $H^+$-ATPase inhibitors; osteoprotegrin; Tibolone; p38 inhibitors; prostanoids; PPAR gamma antagonists or isoflavinoids (e.g., genistein and ipriflavone); androgens (e.g., testosterone and dihydrotestosterone); RANK ligand antagonists; TRAP inhibitors; AP-1 inhibitors and progesterone receptor agonists (e.g., medroxyprogesterone acetate (MPA)).

Examples of suitable cardiovascular agents for use in combination with the compounds of the present invention include vasopeptidase inhibitors, ACE inhibitors, α-reductase inhibitors, muscarinic Ach antagonists, acetylcholinesterase inhibitors, angiotensin II receptor antagonists, thrombin inhibitors, Factor Xa inhibitors, tissue plasminogen activators, streptokinase, or other thrombolytic or antithrombotic agents.

Compounds of formula I and their physiologically acceptable salts, prodrug esters or stereoisomers thereof may be formulated for administration via any suitable means, for example, orally, such as in the form of tablets, capsules, granules or powders; rectally, such as in the form of suppositories; nasally, including administration to the nasal membranes, such as by inhalation spray; topically (including buccal and sublingual); vaginal or parental (including intramuscular, sub-cutaneous, intravenous, and directly into the affected tissue) administration or in a form suitable for administration by inhalation or insufflation. The formulations may, where appropriate, be conveniently presented in discrete dosage units and may be prepared by any of the methods well known in the art of pharmacy. All methods may include the step of bringing into association the active compound with liquid carriers or finely divided solid carriers, or both, and then if necessary, shaping the product into the desired formulation.

The active principle may be in the form of a solid or a liquid and can be utilized in a composition such as tablet, capsule, ointment, solution or suspension, or in other suitable carrier materials. Examples of suitable carrier materials are iontophoetic devices, rectal suppositories, transdermal systems, granules, injectable preparations, or the like, prepared according to procedures known in the art. Further, the active principle comprising a pharmaceutically effective amount of at least one compound of formula I, either alone or in combination, or in combination with one or more other active agent(s) may be incorporated with excipients normally employed in therapeutic medicines, such as talc, gum arabic, lactose, starch, magnesium stearate, polyuidone, cellulose derivatives, cacao butter, semisynthetic glycerides, aqueous or non-aqueous vehicles, fats of animal or vegetable origin, glycols, various wetting agents, dispersants or emulsifiers, silicone gels, stabilizers, certain polymers or copolymers, preservatives, binders, flavorings, colors and the like, as called for by acceptable pharmaceutical practice.

Dosage of the active principle required for use in treatment may vary not only with the particular compound selected, but also with the route of administration, the nature of the condition being treated and the age and condition of the patient. In general, however, a suitable dose will be in the range of from about 0.0002 to 300 mg/kg of body weight per day, particularly from about 0.02 to 50 mg/kg of body weight per day, on a regimen of single or 2 to 4 divided daily doses. For example, for an adult with an average weight of 60 to 70 Kg, the dosage of active principle can vary between 1 and 500 mg when administered orally, in one or more daily doses, or from 0.01 to 50 mg, when administered parenterally in one or more daily dosages.

The above other therapeutic agents, when employed in combination with the compounds of the present invention, may be used, for example, in those amounts indicated in the Physicians' Desk Reference (PDR) or as otherwise determined by one of ordinary skill in the art.

The following examples serve to better illustrate, but not limit, some of the preferred embodiments of the invention.

EXAMPLE 1

4,6-dimethoxyindole-2,3-dione

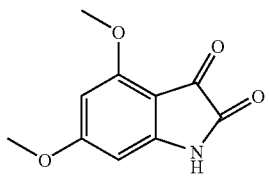

12 g (63 mmol) of 3,5-dimethoxyaniline hydrochloride and 20 ml (230 mol) of oxalyl chloride were stirred at 165° C. for 30 min. The excess of oxalyl chloride was distilled (the color of the reaction mixture changed from dark-red to green-yellow). The reaction mixture was cooled and methanol was added. The resulting suspension was heated then filtered, washed with methanol and dried to yield 13 g of 4,6-dimethoxyindole-2,3-dione (100% yield).

$C_{10}H_9NO_4$=207.19 g/mol; ESI-LC/MS $(M+H)^+$=208; MP: 300-304° C; $^1H$ NMR (400 MHz, DMSO-$d_6$): δ 10.9 (bs, 1H), 6.16 (d, J=1.76 Hz, 1H), 6.00 (d, J=1.76 Hz, 1H), 3.91 (s, 3H), 3.88 (s, 3H).

EXAMPLE 2

4,6-dimethoxyanthranilic acid

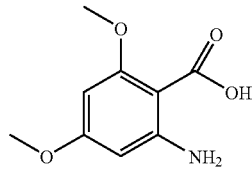

To a heated mixture (in an oversized flask) of 13 g (63 mmol) 4,6-dimethoxyindole-2,3-dione prepared in Example 1 and 108 ml of 33% NaOH solution was carefully added 20 ml of a 30% solution of $H_2O_2$. A vigorous exothermic reaction occurs. After all $H_2O_2$ was added, the reaction mixture was maintained at 100° C. for an additional 10 min. The pH of the solution was brought to 8 with concentrated HCl and acidified to pH 5-6 with acetic acid. The solid was filtered, washed with water and dried to yield 6.2 g of 4,6-dimethoxyanthranilic acid as a pale brown solid (50% yield).

$C_9H_{11}NO_4$=197.19 g/mol; HPLC purity=100%; ESI-LC/MS $(M+H)^+$=198.: MP: 120-125° C.; $^1H$ NMR (400 MHz, DMSO-$d_6$): δ 5.94 (d, J=1.76 Hz, 1H), 5.79 (d, J=1.76 Hz, 1H), 3.75 (s, 3H), 3.71 (s, 3H).

EXAMPLE 3

Methyl 2-amino-4,6-dimethoxybenzoate

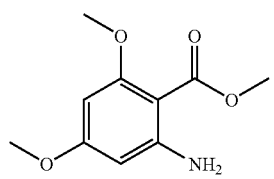

To a mixture of 0.627 g (3.18 mmol) of the 4,6-dimethoxy-anthranilic acid prepared in Example 2, 7 ml of MeOH, and 7 ml of THF, was added 8 ml of trimethylsilyl-diazomethane. After standing overnight at room temperature, the mixture was concentrated to yield quantitatively the corresponding methyl ester. The product was used without any further purification in the following step.

$C_{10}H_{13}NO_4$=211.22 g/mol; HPLC purity=85%; ESI-LC/MS $(M+H)^+$=212; $^1H$ NMR 400 MHz, CDCl$_3$): δ 3.71 (s, 3H); 3.75 (s, 3H); 3.82 (s, 3H); 5.74 (d, 1H); 5.78 (d, 1H).

EXAMPLE 4

5,7-dimethoxy-3,1-benzoxazine-4-one

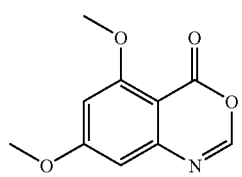

A mixture of 1.0 g (5.07 mmol) of 4,6-dimethoxy-anthranilic acid, as prepared in Example 3, and 15 ml of triethylorthoformate (90.2 mmol) was heated to 140° C. for 4 h. The volatiles were evaporated under reduced pressure to give 0.8 g of 5,7-dimethoxy-3,1-benzoxazine-4-one as a yellow solid (76% yield), which was used without any further purification.

$C_{10}H_9NO_4$=207.19 g/mol.

EXAMPLE 5

1,2-dihydro-5,7-dimethoxy-3,1-benzoxazine-2,4-dione (4,6-dimethoxyisatoic anhydride)

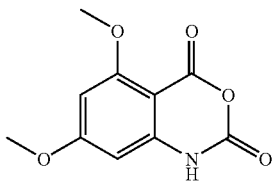

To a cooled (0° C.) brown solution of 4,6-dimethoxy anthranilic acid (76.0 g, 0.385 mol), prepared as in Example 2, in tetrahydrofuran (1.3 L) was added triphosgene (40.0 g, 0.135 mol) in portions over a 20 min period. After 30 min, the reaction was warmed to room temperature and stirred for an additional 1.5 h. The reaction mixture was poured into an Erlenmeyer flask containing water and cooled to 0° C. with an ice bath. Additional water was added to facilitate the stirring of the thick solid formed. After stirring for 30 min, the reaction mixture was filtered to give a beige solid. The solid was washed with water, air-dried, and then dried under high vacuum to give 79.2 g (92%) of the isatoic anhydride.

$C_{10}H_9NO_5$=223.18 g/mol; HPLC purity=>96%; ESI-LC/MS (M−H)⁻=221.9.: MP: 287-293° C. decomposes; $^1$H NMR (400 MHz, DMSO-d$_6$): δ 11.51 (bs, 1H), 6.36 (d, J=1.76 Hz, 1H), 6.20 (d, J=1.76 Hz, 1H), 3.86 (s, 3H), 3.85 (s, 3H).

EXAMPLE 6

5,7-dimethoxy-2-methyl-3,1-benzoxazine-4-one

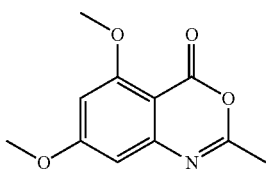

The anthranilic acid (388 mg, 1.97 mmol) prepared in Example 2 was taken up in anhydrous methylene chloride (10 mL). Triethylamine (2.36 mmol) was added followed by addition of acetic anhydride (2.36 mmol). The reaction mixture was heated at 40° C. for 18 hours. Subsequently, the reaction mixture was poured into water and extracted with methylene chloride. The organic layer was washed with saturated aqueous sodium bicarbonate, brine, dried over magnesium sulfate, filtered, and concentrated in vacuo to afford 5,7-dimethoxy-2-methyl-3,1-benzoxazine-4-one (51% yield).

$C_{11}H_{11}NO_4$=221.21 g/mol; HPLC purity=75%; ESI-LC/MS (M+H)⁺=222.07; $^1$H NMR (400 MHz, DMSO-d$_6$): δ 6.58 (d, J=1.76 Hz, 1H), 6.46 (d, J=1.76 Hz, 1H), 3.84 (s, 3H), 3.80 (s, 3H), 2.24 (s, 3H).

EXAMPLE 7

5,7-dimethoxy-2-ethyl-3,1-benzoxazine-4-one

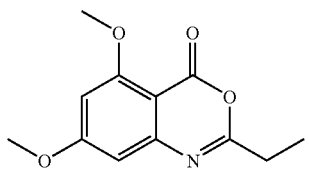

To a mixture of anthranilic acid (207 mg, 1.05 mmol), as prepared in Example 2, and 3 mL anhydrous methylene chloride, was added triethylamine (2.73 mmol). The mixture was cooled to 0° C. Propionyl chloride (2.52 mmol) was added dropwise to the reaction mixture. The solution was allowed to warm to ambient temperature over two hours. The reaction mixture was quenched with water and extracted twice with methylene chloride. The combined organic extracts were washed with brine, dried over magnesium sulfate, filtered and concentrated in vacuo to afford 5,7-dimethoxy-2-ethyl-3,1-benzoxazine-4-one (83% yield).

$C_{12}H_{13}NO_4$=235.24 g/mol; HPLC purity=>99%; ESI-LC/MS (M+H)⁺=236.09. $^1$H NMR (CDCl$_3$, 400 MHz): δ 1.33 (3H, t, J=7.5 Hz), 2.66 (2H, q, J=7.5 Hz), 3.91 (3H, s), 3.97 (3H, s), 6.46 (1H, d, J=2.2 Hz), 6.61 (1H, d, J=2.2 Hz).

According to the method described in Example 7 and by using the appropriate acid chlorides, the following compounds of examples 8 to 11 were prepared.

EXAMPLE 8

5,7-dimethoxy-2-n-propyl-3,1-benzoxazine-4-one

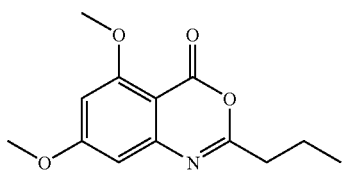

$C_{13}H_{15}NO_4$=249.26 g/mol; HPLC purity=90%; ESI-LC/MS (M+H)⁺=250.09; $^1$H NMR (CDCl$_3$): δ 1.00 (3H, t, J=7.5 Hz), 1.83 (2H, m), 2.61 (2H, t, J=7.5 Hz), 3.91 (3H, s), 3.96 (3H, s), 6.46 (1H, d, J=2.2 Hz), 6.61 (1H, d, J=2.2 Hz).

EXAMPLE 9

5,7-dimethoxy-2-isopropyl-3,1-benzoxazine-4-one

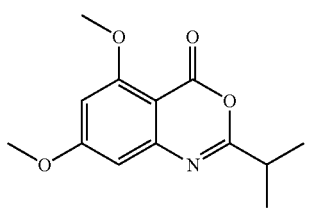

$C_{13}H_{15}NO_4$=249.26 g/mol; HPLC purity=90%; ESI-LC/MS (M+H)$^+$=250.08. $^1$H NMR (CDCl$_3$, 400 MHz): δ 1.34 (6H, d, J=7.0 Hz), 2.87(1H, septet, J=7.0 Hz), 3.91 (3H, s), 3.96 (3H, s), 6.46 (1H, d, J=2.2 Hz), 6.62 (1H, d, J=2.2 Hz)

EXAMPLE 10

5,7-dimethoxy-2-n-butyl-3,1-benzoxazine-4-one

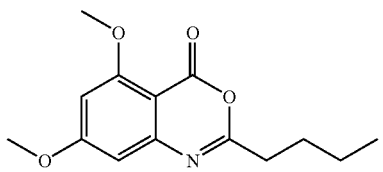

$C_{14}H_{17}NO_4$=263.29 g/mol; HPLC purity=95%; ESI-LC/MS (M+H)$^+$=264.4; $^1$H NMR (CDCl$_3$): δ 0.95 (3H, t, J=7.3 Hz), 1.42 (2H, m) 1.78 (2H, m), 2.62 (2H, t, J=7.7 Hz), 3.91 (3H, s), 3.97 (3H, s), 6.46 (1H, d, J=2.2 Hz), 6.60 (1H, d, J=2.2 Hz).

EXAMPLE 11

5,7-dimethoxy-2-isobutyl-3,1-benzoxazine-4-one

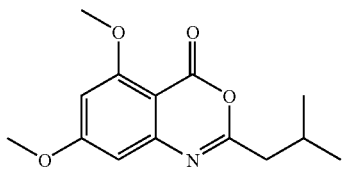

$C_{14}H_{17}NO_4$=263.29 g/mol; HPLC purity=94%; ESI-LC/MS (M+H)$^+$=264.08; $^1$H NMR (CDCl$_3$): δ 1.02 (6H, d, J=7.04 Hz), 2.29 (1H, m) 2.50 (2H, d, J=7.5 Hz), 3.91 (3H, s), 3.97 (3H, s), 6.46 (1H, d, J=2.2 Hz), 6.63 (1H, d, J=2.2 Hz).

EXAMPLE 12

Benzamide, 2-amino-4,6-dimethoxy-N-(4-methoxy-2-methylphenyl)

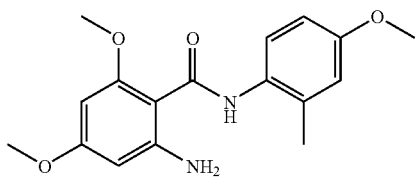

To a mixture of 150 mg (0.673 mmol) of the isatoic anhydride prepared in Example 5, 184 mg (1.34 mmol) of 4-methoxy-2-methylaniline and a catalytic amount of 4-dimethylaminopyridine (5 mg) at room temperature was added N,N-dimethylacetamide (1.5 mL). The mixture was heated at 110° C. under nitrogen atmosphere overnight, then cooled to room temperature. Solvent was removed in vacuo, and the residue was partitioned between EtOAc and water. The aqueous layer was extracted with EtOAc twice and the combined organic layers were washed with water and brine, dried over Na$_2$SO$_4$, and concentrated. The residue was dissolved in CH$_2$Cl$_2$ containing a small amount of methanol and chromatographed on silica using 35% EtOAc in hexane as eluent. A total of 155 mg (72%) of a pink solid was obtained.

$C_{17}H_{20}N_2O_4$=316 g/mol; HPLC purity=84%; ESI-LC/MS (M+H)$^+$=317.

EXAMPLE 13

Benzamide, 2-amino-4,6-dimethoxy-N-(2-fluoro-4-methoxyphenyl)

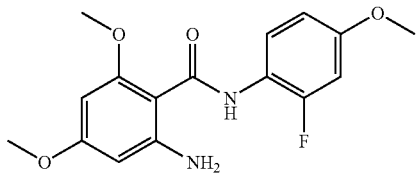

To a mixture of 200 mg (1.42 mmol) of 4-amino-3-fluoroanisole and 1M sodium bis(trimethylsilyl)amide (4.39 mmol) in THF solution at room temperature under nitrogen atmosphere, 320 mg (1.42 mmol) of the isatoic anhydride prepared in Example 5, was added followed by the addition of 2 mL of N,N-dimethylacetamide. The suspension was heated at 90° C. for 4 hours. After completion of the reaction, as monitored by HPLC, the mixture was cooled to room temperature, diluted with EtOAc and 1N HCl, and the resulting layers were separated. The aqueous layer was extracted with EtOAc twice, and the combined organic extracts were washed with water, saturated NaHCO$_3$, brine, dried over Na$_2$SO$_4$ and concentrated. The residue was dissolved in CH$_2$Cl$_2$ and chromatographed on silica using 30% EtOAc in hexane as eluent. A total of 220 mg (48%) of a yellow solid was obtained.

$C_{16}H_{17}FN_2O_4$=320 g/mol; ESI-LC/MS (M+H)$^+$=321.1; $^1$H NMR (400 MHz, CDCl$_3$): δ 10.0 (1H, s), 8.26 (1H, t, J=8.8 Hz), 6.70 (2H, m), 6.42 (2H, broad), 5.85 (1H, d, J=2.6 Hz), 5.82 (1H, d, J=2.6 Hz), 3.94 (3H, s), 3.79 (6H, s).

According to the procedures described in either Examples 12 or 13, and by the reaction of the appropriated anilines on the corresponding isatoic anhydrate, the following compounds in Examples 14 to 16 were prepared.

EXAMPLE 14

Benzamide, 2-amino-4,6-dimethoxy-N-(3-fluoro-4-methoxyphenyl)

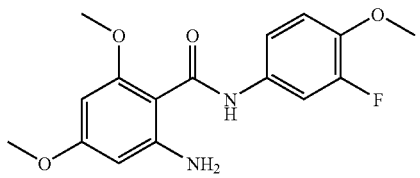

Used directly without any further purification by column chromatography.

$C_{16}H_{17}FN_2O_4$=320 g/mol; ESI-LC/MS (M+H)$^+$=321.1.

EXAMPLE 15

Benzamide, 2-amino-4,6-dimethoxy-N-(3-chloro-4-hydroxyphenyl)

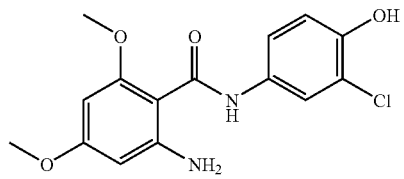

Purified by column chromatography, using 40% EtOAc in hexane as eluent. (52% yield).

$C_{15}H_{15}ClN_2O_4$=322 g/mol; ESI-LC/MS (M+H)$^+$=323.1.

EXAMPLE 16

Benzamide, 2-amino-4,6-dimethoxy-N-(2-chloro-4-methoxyphenyl)

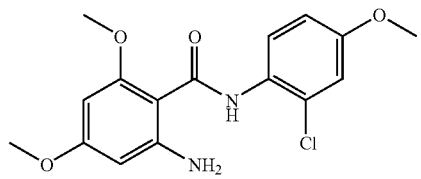

Purified by column chromatography using 30% EtOAc in hexane as eluent. (68% yield)

$C_{16}H_{17}ClN_2O_4$=336 g/mol; ESI-LC/MS (M+H)$^+$=337.0.

EXAMPLE 17

5,7-dimethoxy-3-(4-methoxy-2-methylphenyl)-4(3H)-quinazolinone

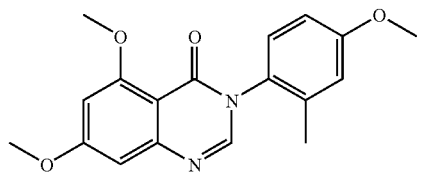

A suspension of 150 mg (0.475 mmol) of the compound prepared in Example 12 in triethylorthoformate (5 ml) was heated to reflux under $N_2$ for 5 hours. HPLC showed reaction was complete. The solvent was removed in vacuo to give a pink solid. The residue was dissolved in $CH_2Cl_2$ and chromatographed on silica using 70% EtOAc in hexane as eluent. A total of 140 mg (90% yield) of 5,7-dimethoxy-3-(4-methoxy-2-methylphenyl)-4(3H)-quinazolinone was obtained as an off-white solid.

$C_{18}H_{18}N_2O_4$=326 g/mol; ESI-LC/MS (M+H)$^+$=327.1; $^1$H NMR (400 MHz, CDCl$_3$): δ 7.90 (1H, s), 7.12 (1H, d, J=8.8 Hz), 6.87 (1H, d, J=2.6 Hz), 6.83 (1H, dd, J=2.6 Hz and J=8.8 Hz), 6.76 (1H, d, J=2.2 Hz), 6.51 (1H, d, J=2.2 Hz), 3.94 (6H, s), 3.84 (3H,s) 2.1 (3H, s).

EXAMPLE 18

5,7-dimethoxy-3-(4-methoxyphenyl)-4(3H)-quinazolinone

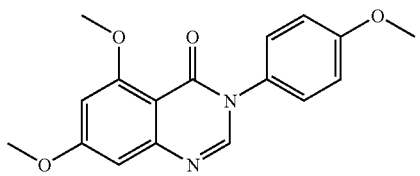

A mixture of 200 mg (0.97 mmol) of the benzoxazinone prepared in Example 4 and 119 mg (0.97 mmol) of p-anisidine in 5 ml of xylene was refluxed for 4 hours. The solvent was removed and the target compound purified by flash chromatography on silica gel (loaded with $CH_2Cl_2$ and eluted with 40% EtOAc in hexane) to obtain 120 mg of 5,7-dimethoxy-3-(4-methoxyphenyl)-4(3H)-quinazolinone (40% yield) as a white solid.

$C_{17}H_{16}N_2O_4$=312.33 g/mol; ESI-LC/MS (M+H)$^+$=313; $^1$H NMR (400 MHz, DMSO-d$_6$): δ 8.17 (1H, s), 7.36 (1H, d, J=8.8 Hz), 7.06 (1H, d, J=8.8 Hz), 6.73 (1H, d, J=2.2 Hz), 6.61 (1H, d, J=2.2 Hz), 3.9 (s, 3H), 3.83 (s, 3H), 3.82 (s, 3H).

EXAMPLE 19

5,7-dimethoxy-3-(4-methoxyphenyl)-4(3H)-quinazolinone

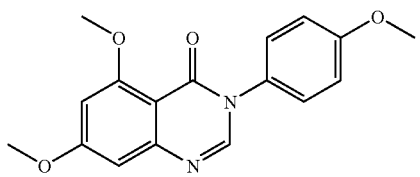

A mixture of 50 g (0.224 mol) of the isatoic anhydride as prepared in Example 5, 68.9 g (0.560 mol) of p-anisidine, 2.73 g (0.022 mol) of N,N-dimethylamino pyridine, and 500 mL of anhydrous dimethylacetamide, was warmed to 110° C. A clear brown solution formed at 80-90° C. and bubbling was observed (CO$_2$ loss). After 24 hr, the reaction was cooled to room temperature, diluted with water (1L), and extracted with EtOAc (3×500 mL). The combined organic layers were washed with brine (1×250 mL), dried over MgSO$_4$, filtered, and concentrated to give a brown residue weighing 85.2 g. The brown residue was dissolved in anhydrous triethylorthoformate (720 mL) and warmed to reflux for 4 hr. Upon cooling to room temperature, an off-white solid precipitated. Filtration, washing with triethylorthoformate (1×1 L), air drying, and drying under high vacuum gave 55.1 g (79%) of 5,7-dimethoxy-3-(4-methoxyphenyl)quinazoline-4-one, as an off-white solid.

$C_{17}H_{16}N_2O_4$=312.33 g/mol; HPLC purity=>98%; ESI-LC/MS (M+H)$^+$=313.1; $^1$H NMR (400 MHz, DMSO-d$_6$): δ

8.17 (s, 1H), 7.37 (d, 2H, J=8.8 Hz), 7.06 (d, 2H, J=8.8 Hz), 6.73 (d, 1H, J=2.2 Hz), 6.62 (d, 1H, J=2.2 Hz), 3.9 (s, 3H), 3.83 (s, 3H), 3.82 (s, 3H).

EXAMPLE 20

5,7-dimethoxy-2-methyl-3-(4-methoxyphenyl)-4(3H)-quinazolinone

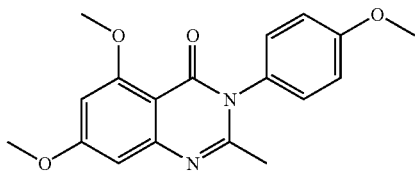

To a mixture of 135.5 mg (0.612 mmol) of the benzoxazinone prepared in Example 6 and glacial acetic acid (2 mL), p-anisidine (0.735 mmol) was added and the reaction mixture was heated to 60° C. for 24 hrs. The reaction mixture was concentrated in vacuo and partitioned between ethyl acetate and saturated aqueous sodium bicarbonate. The organic layer was washed with water, brine, dried over magnesium sulfate, filtered, and concentrated in vacuo to afford the product as a yellow oil (13.7% yield).

$C_{18}H_{18}N_2O_4$=326.36 g/mol; HPLC purity=>99%; ESI-LC/MS (M+H)$^+$=327.0; $^1$H NMR (CDCl$_3$): δ 2.19 (3H, s, methyl), 3.86 (3H, s), 3.90 (3H, s), 3.91 (3H, s), 6.43 (1H, d, J=2.2 Hz), 6.68 (1H, d, J=2.2 Hz), 7.01 (2H, d, J=8.8 Hz), 7.13 (2H, d, J=8.8 Hz).

EXAMPLE 21

2-mercapto-5,7-dimethoxy-3-(4-methoxyphenyl)-4(3H)-quinazolinone

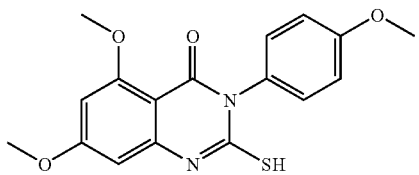

The Example 3 compound (0.675 g, 3.19 mmol) was refluxed in 20 ml of toluene with 0.525 g (3.2 mmol) of 4-methoxyphenylisothiocyanate for 15 h. The solvent was evaporated and the residue triturated with MeOH/CH$_2$Cl$_2$ to yield 0.537 g of 2-mercapto-5,7-dimethoxy-3-(4-methoxyphenyl)-4(3H)-quinazolinone (49%) as an off-white solid.

$C_{17}H_{16}N_2O_4S$=344.39 g/mol; HPLC purity=91.7%; ESI-LC/MS (M+H)$^+$=345.2; MP: 322-326° C.; $^1$H NMR (CDCl$_3$): δ 3.85 (3H, s), 3.9 (3H, s), 3.91 (3H, s), 6.06 (1H, d, J=2.1 Hz), 6.08 (1H, d, J=2.1 Hz), 7.02 (1H, d, J=8.6 Hz), 7.16 (2H, d, J=8.6 Hz), 9.38 (1H, s).

EXAMPLE 22

5,7-dimethoxy-3-(4-methoxyphenyl)-2,4(1H,3H)-quinazoline-dione

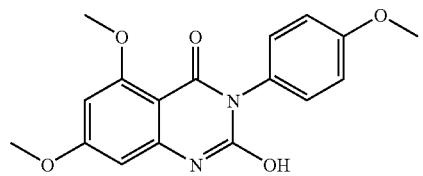

The previously prepared anthranilic acid from Example 2 (489 mg, 2.48 mmol) was dissolved in 20 ml of anhydrous ethyl acetate and stirred over 100 mg of 4 Å molecular sieves. 4-methoxybenzoic isocyanate (2.48 mmol) was added and the reaction mixture was heated to reflux for one hour. The reaction mixture was cooled to ambient temperature. Subsequently, the reaction mixture was filtered to remove the molecular sieves. The solvent was removed in vacuo to afford a mixture of uncyclized product and cyclized product. The crude mixture was taken up in ethanol and saturated with hydrochloric acid. The reaction mixture was heated to reflux for two hours, then allowed to cool to ambient temperature. The resulting mixture was purified by silica column (elution with 50% ethyl acetate in hexanes) to afford the pure product (59% yield).

$C_{17}H_{16}N_2O_5$=328.32 g/mol; ESI-LC/MS (M+H)$^+$=329.13; ESI-LC/MS (M−H)$^-$327.07 $^1$H NMR (DMSO-d$_6$): δ 3.78 (3H, s), 3.79 (3H, s), 3.83 (3H, s), 6.28 (1H, d, J=2.2 Hz), 6.31 (1H, d, J=2.2 Hz), 6.98 (2H, d, J=8.8 Hz), 7.12 (2H, d, J=8.8 Hz), 11.25 (1H, s).

According to any of the procedures described in Examples 17 to 22, and by reacting the appropriate amino compounds with the corresponding benzamide, benzoxazinone, isatoic anhydride or anthranilic acid derivatives, the following compounds described in Examples 23 to 32 were prepared.

EXAMPLE 23

3-(3-chloro-4-hydroxyphenyl)-5,7-dimethoxy-4(3H)-quinazolinone

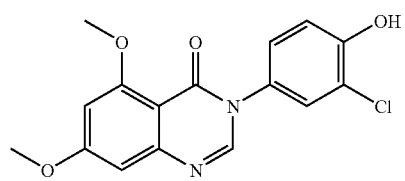

$C_{17}H_{15}ClN_2O_4$=346 g/mol; HPLC purity=95.7%.

EXAMPLE 24

5,7-dimethoxy-3-(3-fluoro-4-methoxyphenyl)-4(3H)-quinazolinone

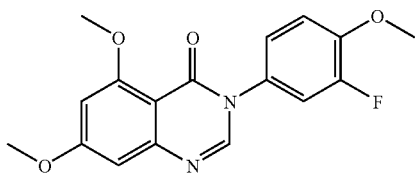

$C_{17}H_{15}FN_2O_4$=330 g/mol; HPLC purity=94%; ESI-LC/MS (M+H)$^+$=331.1; $^1$H NMR (400 MHz, CDCl$_3$): δ 8.00 (1H, s), 7.20 (1H, dd, J=11.4 Hz), 7.12–7.04 (2H, m), 6.75 (1H, d, J=2.5 Hz), 6.51 (1H, d, J=2.2 Hz), 3.95 (6H, s), 3.93 (3H, s).

EXAMPLE 25

5,7-dimethoxy-3-(6-methoxy-3-pyridinyl)-4(3H)-quinazolinone

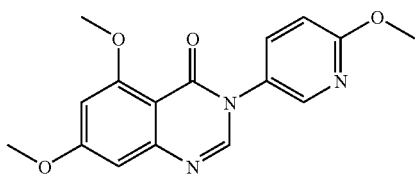

$C_{16}H_{15}N_3O_4$=313 g/mol; HPLC purity=95%; ESI-LC/MS (M+H)$^+$314; $^1$H NMR (DMSO-d$_6$): δ 8.27 (1H, d, J=2.6 Hz), 8.23 (1H, s), 7.84 (1H, q, J=8.8 Hz and J=2.6 Hz), 6.97 (1H, d, J=8.8 Hz), 6.74 (1H, d, J=2.2 Hz), 6.63 (1H, d, J=2.2 Hz), 3.91 (3H, s), 3.90 (3H, s), 3.83 (3H, s).

EXAMPLE 26

5,7-dimethoxy-3-(3-fluoro-4-methoxyphenyl)-4(3H)-quinazolinone

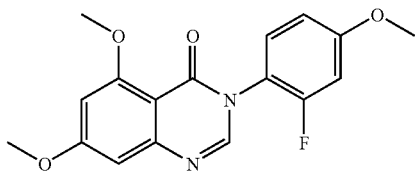

$C_{17}H_{15}FN_2O_4$=330 g/mol; HPLC purity=100%; ESI-LC/MS (M+H)$^+$=331.1; $^1$H NMR (400 MHz, CDCl$_3$): δ 7.93 (1H, d, J=0.9 Hz), 7.27–7.25 (1H, m), 6.81–6.78 (2H, m), 6.76 (1H, d, J=2.2 Hz), 6.51 (1H, d, J=2.2 Hz), 3.94 (3H, s), 3.93 (3H, s), 3.86 (3H, s).

EXAMPLE 27

3-(3-chloro-4-methoxyphenyl)-5,7-dimethoxy-4(3H)-quinazolinone

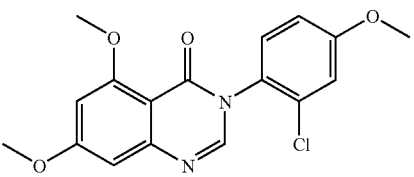

$C_{17}H_{15}ClN_2O_4$ 346 g/mol; HPLC purity 95%; ESI-LC/MS (M+H)$^+$=347.05; $^1$H NMR (400 MHz, CDCl$_3$): δ 7.87 (1H, s), 7.30 (1H, d, J=8.8 Hz), 7.09 (1H, d, J=2.6 Hz), 6.93 (1H, dd, J=2.6 Hz and J=8.8 Hz), 6.77 (1H, d, J=2.6 Hz), 6.51 (1H, d, J=2.2 Hz), 3.94 (6H, s), 3.86 (3H, s).

EXAMPLE 28

5,7-dimethoxy-2-ethyl-3-(4-methoxyphenol)quinazoline-4-one

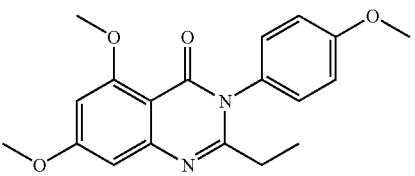

$C_{19}H_{20}N_2O_4$=340.37 g/mol; HPLC purity=93%; $^1$H NMR (CDCl$_3$): δ 1.18 (3H, t, J=7.4 Hz), 2.45 (2H, q, J=7.4 Hz), 3.86 (3H, s), 3.9 (3H, s), 3.93 (3H, s), 6.43 (1H, d, J=1.8 Hz), 6.79 (1H, d, J=1.8 Hz), 7.01 (2H, d, J=8.8 Hz), 7.13 (2H, d, J=8.8 Hz).

EXAMPLE 29

5,7-dimethoxy-2-propyl-3-(4-methoxyphenol)quinazoline-4-one

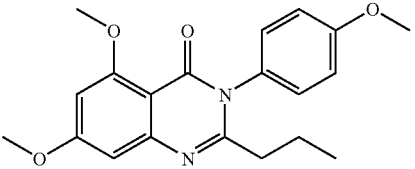

$C_{20}H_{22}N_2O_4$=354.4 g/mol; HPLC purity=>99%; ESI-LC/MS (M+H)$^+$=355.1. $^1$H NMR (CDCl$_3$, 400 MHz): δ 0.92 (3H, t, J=7.5 Hz), 1.72 (2H, m), 2.86 (2H, t, J=7.9 Hz), 3.9 (3H, s), 3.94 (3H, s), 3.98 (3H, s), 6.56 (1H, d, J=2.2 Hz), 7.08 (2H, d, J=9 Hz), 7.17 (2H, d, J=9 Hz), 7.21 (1H, d, J=2.2 Hz).

EXAMPLE 30

5,7-dimethoxy-2-isopropyl-3-(4-methoxyphenol)quinazoline-4-one

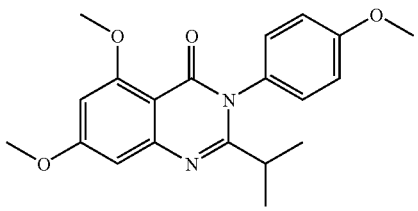

C$_{20}$H$_{22}$N$_2$O$_4$ 354.4 g/mol; HPLC purity=90%; $^1$H NMR (CDCl$_3$): δ 1.19 (6H, d, J=7 Hz), 2.70 (1H, septet, J=7 Hz), 3.86 (3H, s), 3.89 (3H, s), 3.93 (3H, s), 6.41 (1H, d, J=2.2 Hz), 6.72 (1H, d, J=2.2 Hz), 7.00 (2H, d, J=8.8 Hz), 7.12 (2H, d, J=8.8 Hz).

EXAMPLE 31

5,7-dimethoxy-2-butyl-3-(4-methoxyphenol)quinazoline-4-one

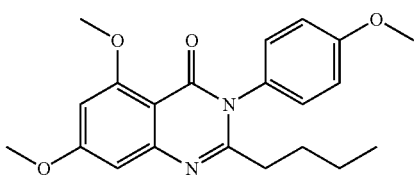

C$_{21}$H$_{24}$N$_2$O$_4$=368.43 g/mol; HPLC purity=89%; ESI-LC/MS (M+H)$^+$=369.11. $^1$H NMR (CDCl$_3$, 400 MHz): δ 0.81 (3H, t, J=7.5 Hz), 1.25 (2H, m), 1.63 (2H, m), 2.39 (2H, t, J=7.9 Hz), 3.86 (3H, S), 3.89 (3H, S), 3.92 (3H, S), 6.42 (1H, d, J=2.2 Hz), 6.71 (1H, d, J=2.2 Hz), 7.01 (2H, d, J=8.8 Hz), 7.13 (2H, d, J=8.8 Hz).

EXAMPLE 32

5,7-dimethoxy-2-isobutyl-3-(4-methoxyphenol)quinazoline-4-one

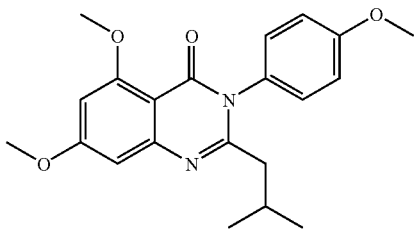

C$_{21}$H$_{24}$N$_2$O$_4$=368.43 g/mol; purity (by NMR)=98%; $^1$H NMR (CDCl$_3$): δ 0.92 (6H, d, J=6.6 Hz), 2.03 (1H, m), 2.83 (2H, d, J=7.44 Hz), 3.89 (3H, s), 3.94 (3H, s), 3.98 (3H, s), 6.56 (1H, d, J=1.8 Hz), 7.07 (2H, d, J=8.8 Hz), 7.15 (2H, d, J=8.8 Hz), 7.30 (1H, d, J=1.8 Hz).

EXAMPLE 33

5,7-dimethoxy-3-(4-methoxyphenyl)-4(3H)-quinazolinethione

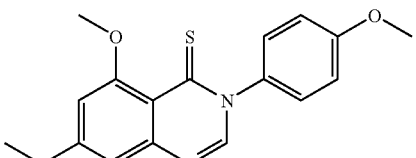

The mixture of 5,7-dimethoxy-3-(4-methoxyphenyl)-quinazoline-4-one (240 mg, 0.76 mmol), as prepared in Example 18 or 19, and Lawesson's reagent (310 mg, 0.76 mmol) in toluene (4 mL) was refluxed overnight. The mixture was evaporated to dryness. EtOAc was added and the mixture was washed with water, brine and dried over MgSO$_4$. Evaporation gave a crude solid. Purification was performed by flash chromatography on silica gel, loaded with dichloromethane and eluted with 45% ethyl acetate in hexane. The pure fraction was combined and evaporated to give a yellow foam (180 mg, 72%).

C$_{17}$H$_{16}$N$_2$O$_3$S=328 g/mol; HPLC purity=95%; ESI-LC/MS (M+H)$^+$=329; $^1$H NMR (500 MHz, CDCl$_3$): δ 8.08 (1H, s), 7.20 (1H, d, J=8.8 Hz), 7.00 (1H, d, J=8.8 Hz), 6.71 (1H, d, J=2.2 Hz), 6.52 (1H, d, J=2.2 Hz), 3.9 (3H, s), 3.83 (3H, s), 3.82 (3H, s).

EXAMPLE 34

5,7-dimethoxy-3-(4-methoxyphenyl)-2-(methylthio)-4(3H)-quinazolinone

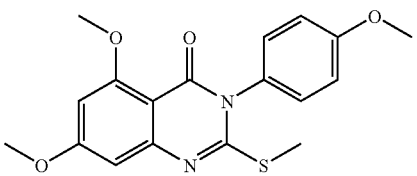

A mixture of 171 mg (0.497 mmol) of the Example 21 compound, 15 ml of MeOH, and 1 ml of 1N NaOH solution, was heated gently until a clear solution was obtained. 295 mg (2 mmol) of methyl iodide was then added and stirring was continued at room temperature for three days. The precipitate was filtered to yield 89.9 mg of 5,7-dimethoxy-2-methylthio-3-(4-methoxyphenyl)-quinazoline-4-one as an off-white solid (50% yield).

C$_{18}$H$_{18}$N$_2$O$_4$S=358.099 g/mol; HPLC purity=99%; ESI-LC/MS (M+H)$^+$=358.9; MP: 212-215° C.; $^1$H NMR (CDCl$_3$): δ 2.49 (3H, s), 3.86 (3H, s), 3.9 (3H, s), 3.92 (3H, s), 6.38 (1H, d, J=2.4 Hz), 6.64 (1H, d, J=2.4 Hz), 7.00 (1H, d, J=8.9 Hz), 7.17 (2H, d, J=8.9 Hz).

EXAMPLE 35

5,7-dihydroxy-3-(4-hydroxyphenyl)-4(3H)-quinazolinone

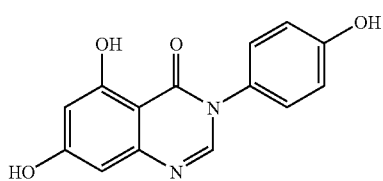

To an ice-cooled mixture of 365 mg (1.17 mmol) of 5,7-dimethoxy-3-(4-methoxyphenyl)-4(3H)-quinazolinone, prepared according to the procedures described in Example 18 or 19, and 10 ml of $CH_2Cl_2$, 3 ml of $BBr_3$ (31.7 mmol) was added. The mixture was stirred at room temperature for 2 days. The solvent was evaporated, the obtained residue treated with a cold $NaHCO_3$ solution and extracted with EtOAc. The organic layer was washed with water and brine, dried over $MgSO_4$ and evaporated to yield a solid which purification by flash chromatography on silica gel (loaded with $CH_2Cl_2$ and eluted with 66% EtOAc in hexane) gave 165 mg of 5,7-dihydroxy-3-(4-hydroxyphenyl)-4(3H)-quinazolinone (40% yield) as a white solid.

$C_{14}H_{10}N_2O_4$=270.25 g/mol; HPLC purity=93.8%; ESI-LC/MS $(M+H)^+$=271.1; MP: 240-245° C.; $^1$H NMR ($CDCl_3$): δ 6.46 (1H, d, J=2.2 Hz), 6.62 (1H, d, J=2.2 Hz), 7.0 (2H, d, J=8.8 Hz), 7.26 (2H, d, J=8.8 Hz), 8.09 (1H, s).

EXAMPLE 36

5,7-dihydroxy-3-(4-hydroxyphenyl)-4(3H)-quinazolinone

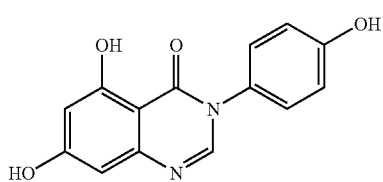

A mixture of 100 mg (0.32 mmol) of 5,7-dimethoxy-3-(4-methoxyphenyl)-4(3H)-quinazolinone as prepared in Example 18 or 19, and 524 mg (6.24 mmol) of sodium ethanethiolate in 2 ml of DMF was refluxed for 3.5 hr. DMF was evaporated and the residue dissolved in water. Concentrated HCl was added to adjust the pH to 5. The precipitate was filtered, dried and purified by chromatography on silica gel (loaded with $CH_2Cl_2$ and a slight amount of MeOH, eluted with 70% EtOAc in hexane) to yield 51 mg of 5,7-dihydroxy-3-(4-hydroxyphenyl)-4(3H)-quinazolinone (59%) as an off-white solid.

This compound has the same characteristics as the compound of Example 35.

EXAMPLE 37

5-hydroxy-7-methoxy-3-(4-methoxyphenyl)quinazoline4-one

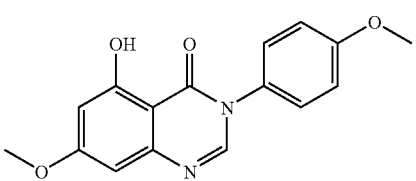

A suspension of 5,7-dimethoxy-3-(4-methoxyphenyl)-4(3H)-quinazolinone (2.40 g, 7.68 mmol), as prepared in Example 18 or 19 and anhydrous lithium chloride (6.51 g, 153.6 mmol) in anhydrous dimethylacetamide (51.2 mL) was warmed to 135° C. After 3 to 5 min the trimethoxy compound goes into solution, then after approximately 10 min a voluminous precipitate formed. The precipitate redissolved after 20 min and the resulting solution was stirred at 135° C. for an additional 2.5 h. Upon cooling to room temperature, the reaction was poured into water (100 mL) and acidified with 1.0N HCl which gave a white precipitate. The mixture was extracted with dichloromethane (3×). The combined organic layers were washed with brine, dried over $MgSO_4$, filtered, and concentrated in vacuo to remove the methylene chloride, leaving a white precipitate in dimethylacetamide. Filtration provided 1.10 g (48% yield) of 5-hydroxy-7-methoxy-3-(4-methoxyphenyl)-4(3H)-quinazolinone, as a white solid.

$C_{16}H_{14}N_2O_4$=298.29 g/mol; HPLC purity 91%; ESI-LC/MS $(M+H)^+$=299.1; $^1$H NMR (400 MHz, DMSO-$d_6$): δ 11.77 (s, 1H), 8.26 (s, 1H) 7.48 (d, J=8.4 Hz, 2H), 7.10 (d, J=8.8 Hz, 2H), 6.72 (d, J=2.2 Hz, 1H), 6.54 (d, J=1.3 Hz, 1H), 3.88 (s, 3H), 3.83 (s, 3H).

According to the procedures described in Examples 35-37, the following compounds described in Example 38 and 39 were prepared.

EXAMPLE 38

5-hydroxy-3-(4-hydroxyphenyl)-7-methoxy-4(3H)-quinazolinone

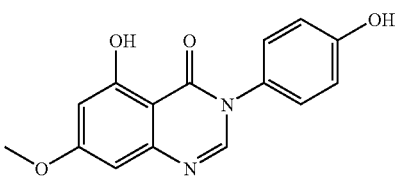

$C_{15}H_{12}N_2O_4$=284.27 g/mol; HPLC purity=98.8%; ESI-LC/MS $(M+H)^+$=$(M+H)^+$=285.2, $(M-H)^-$=283.0; $^1$H NMR (DMSO-$d_6$): δ 11.2 (1H, s), 9.95 (1H, s), 8.22 (1H, s), 7.38 (2H, d, J=8.8 Hz), 6.98 (2H, d, J=8.8 Hz), 6.72 (1H, d, J=2.4 Hz), 6.55 (1H, d, J=2.4 Hz), 3.90 (3H, s).

EXAMPLE 39

2-mercapto-5-hydroxy-3-(4-hydroxyphenyl)-7-methoxy-4(3H)-quinazolinone

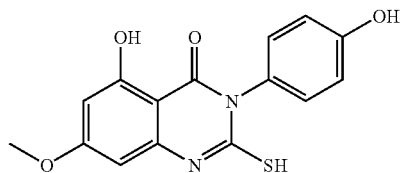

$C_{15}H_{12}N_2O_4S$=316.05 g/mol; HPLC purity=97.5%; ESI-LC/MS (M+H)$^+$=316.8. (M−H)$^−$=314.8; MP: 325-328° C.; $^1$H NMR (CD$_3$OD) δ 7.75 (1H, s), 7.03 (2H, d, J=9.1 Hz), 6.91 (2H, d, J=9.1 Hz), 6.28 (2H, s), 3.88 (3H, s).

EXAMPLE 40

5,7-dihydroxy-3-(4-hydroxyphenyl)quinazoline 4-one trisodium salt

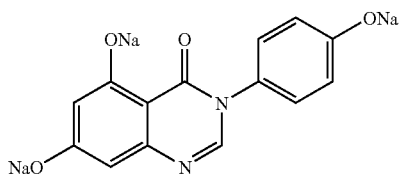

15 mg (0.55 mmol) of the compound prepared in Example 35 or 36 was dissolved in 1.65 ml of 1N NaOH solution while stirring for 30 min. The mixture was lyophilized to give the trisodium salt as a yellowish solid.

$C_{14}H_7N_2Na_3O_4$=336.19 g/mol; HPLC purity=94.2%; ESI-LC/MS (M+H)$^+$=271; $^1$H NMR (CD$_3$OD): δ 6.13 (1H, d, J=2.2 Hz), 6.31 (1H, d, J=2.2 Hz), 6.69 (2H, d, J=8.8 Hz), 6.99 (2H, d, J=8.8 Hz), 7.86 (1H, s).

EXAMPLE 41

5-ethoxy-7-methoxy-3-(4-methoxyphenyl)-4(3H)-quinazolinone

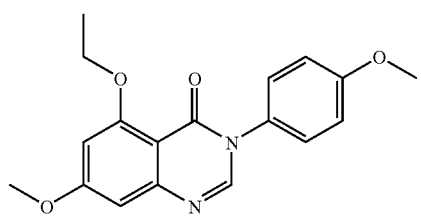

To a suspension of 5-hydroxy-7-methoxy-3-(4-methozyphenyl)-4(3H)-quinazolinone (0.015 g, 0.0503 mmol), as prepared in Example 37, in dimethylformamide (0.26 mL) was added potassium carbonate (0.069 g, 0.503 mmol) and iodoethane (0.040 mL, 0.503 mmol). The reaction vessel was placed in a preheated oil bath (120° C.) and after a few minutes the quinazolinone enters into solution. After 3 h, the reaction was cooled to room temperature and excess iodoethane was removed via rotary evaporation. The reaction mixture was diluted with water (0.75 mL) and extracted with EtOAc (3×). The combined organic layers were washed with brine (1×), dried over MgSO$_4$, filtered, and concentrated to give a yellow solid. Adsorption onto silica gel (60 mg) and column chromatography (1:1 Hexane:EtOAc) provided 0.0080 g (49% yield) of 5-ethoxy-7-methoxy-3-(4-methoxyphenyl)-4-(3H)-quinazolinone as a flaky white solid.

$C_{18}H_{18}N_2O_4$=326.35 g/mol; ESI-LC/MS (M+H)$^+$=327.2; $^1$H NMR (400 MHz, CDCl$_3$): δ 8.0 (s, 1H), 7.29 (d, J=8.8 Hz, 2H), 7.00 (d, J=8.8 Hz, 2H), 6.74 (d, J=2.6 Hz, 1H), 6.48 (d, J=2.6, 1H), 4.12 (q, J=7.0, 2H), 3.92 (s, 3H), 3.85 (s, 3H), 1.52 (t, J=7.0 Hz, 3H).

EXAMPLE 42

5-ethoxy-7-hydroxy-3-(4-hydroxyphenyl)-4(3H)-quinazolinone

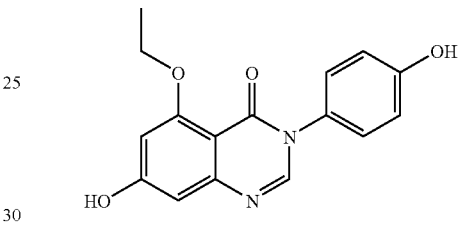

To a solution of 5-ethoxy-7-methoxy-3-(4-methoxyphenyl)-4(3H)-quinazolinone (0.0080 g, 0.0245 mmol), as prepared in Example 41, in dimethylformamide (0.25 mL), was added sodium ethanethiolate (0.0047 g, 0.0563 mmol). The resulting suspension was warmed to 120° C. to form a solution. After each hour (for 7 hours) additional sodium ethanethiolate (0.0047, 0.0563 mmol) was added. After 7 hrs, the cloudy orange reaction solution was cooled to room temperature and diluted with water (0.75 mL). The resulting yellow solution was acidified with 1.0N HCl to pH 3 wherein the reaction solution became cloudy. Extraction was performed with EtOAc (3×) and dichloromethane (3×). The combined organic layers were washed with brine (1×), dried over MgSO$_4$, filtered, and concentrated. Column chromatography (5% MeOH in CH$_2$Cl$_2$) gave 0.0017 g (23%) of 5-ethoxy-7-hydroxy-3-(4-hydroxyphenyl) quinazoline-4-one, as a white solid.

$C_{16}H_{14}N_2O_4$=298 g/mol; HPLC purity=>97%; ESI-LC/MS (M+H)$^+$=299.1; $^1$H NMR (400 MHz, CD$_3$OD) δ: 8.09 (s, 1H), 7.22 (d, J=8.8 Hz, 2H), 6.90 (d, J=8.2 Hz, 2H), 6.61 (d, J=2.2 Hz, 1H), 6.52 (d, J=2.2 Hz, 1H), 4.13 (q, J=7.0 Hz, 2H), 1.44 (t, J=7.0 Hz, 3H).

EXAMPLE 43

7-benzyloxy-5-methoxy-3-(4-benzyloxyphenyl)-4(3H)-quinazolinone

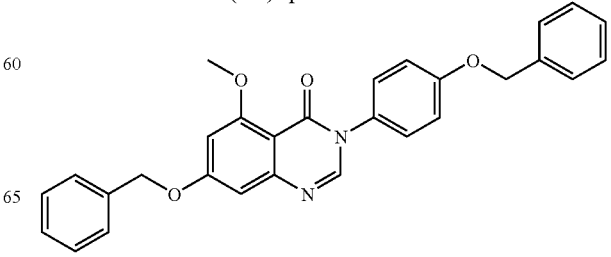

To a cooled (0° C.) clear colorless solution of 5,7-dihydroxy-3-(4-hydroxyphenyl)-4(3H)-quinazolinone (0.330 g, 1.22 mmol), as prepared in Example 35 or 36, in anhydrous dimethylacetamide (18.5 mL), was added sodium hydride (60% dispersion, 0.274 g, 6.85 mmol) portionwise over a 25 min. period. Following the final addition, the reaction mixture was stirred for an additional 30 minutes at 0° C. and then warmed to room temperature for 1.5 h. Over the course of the reaction, the clear reaction solution became a clear, green color with a white precipitate coating the sides of the reaction vessel. Upon recooling to 0° C., benzyl bromide (0.29 mL, 2.44 mmol) was added. The reaction was stirred at 0° C. for 1 hr. wherein the reaction solution became a clear, orange solution. Next, iodomethane (0.14 mL, 2.22 mmol) was added. After 1 h at 0° C., the reaction was allowed to warm to room temperature and stir for 1 h. The reaction was diluted with water (45 mL) and extracted with EtOAc (2×10 mL). The combined organic layers were washed with brine (1×5 mL), dried over MgSO$_4$, filtered, and concentrated to give an orange residue. Column chromatography (1:1 hexane:EtOAc) provided 0.25 g (44%) of the product as a white foam.

$C_{29}H_{24}N_2O_4$=464.5 g/mol; HPLC purity=>95%; ESI-LC/MS (M+H)$^+$=465.2; $^1$H NMR (400 MHz, CDCl$_3$): δ 8.02 (s, 1H), 7.48-7.32 (m, 10H), 7.29 (d, J=9.2 Hz, 2H), 7.07 (d, J=8.8 Hz, 2H) 6.83 (d, J=2.2 Hz, 1H), 6.59 (d, J=2.2 Hz, 1H), 5.18 (s, 2H), 5.12 (s, 2H) 3.93 (s, 3H).

EXAMPLE 44

7-hydroxy-5-methoxy-3-(4-hydroxyphenyl)-4(3H)-quinazolinone

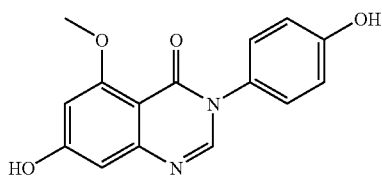

To a solution of the Example 43 compound (0.200 g, 0.430 mmol) in 1:1 EtOAc:ethanol (12.9 mL) was added 10% palladium on carbon (0.100 g). Hydrogen (balloon) was bubbled through the reaction for five minutes to purge the vessel and then the reaction was stirred vigorously under a hydrogen atmosphere for 4 h. The reaction was filtered through Celite® and the eluant was concentrated which gave a white solid weighing 0.122 g. The crude material was adsorbed on silica gel (600 mg). Column chromatography (7.5% MeOH in CH$_2$Cl$_2$) gave 0.015 g (12%) of a white solid.

$C_{15}H_{12}N_2O_4$=284 g/mol; HPLC purity=>95%; ESI-LC/MS (M+H)$^+$=285.; MP: decomposes 240-360° C.; $^1$H NMR (400 MHz, DMSO-d$_6$): δ 8.05 (s, 1H), 7.19 (d, J=8.8 Hz, 2H), 6.85 (d, J=8.4 Hz, 2H), 6.52 (s, 1H), 6.46 (s, 1H), 3.78 (s, 3H).

EXAMPLE 45

5,7-Dihydroxy-3-(4-hydroxyphenyl)-4(3H)-quinazolinethione

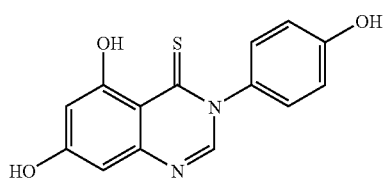

5,7-Dimethoxy-3-(4-methoxyphenyl)-4(3H)-quinazolinethione (6.5 g, 19.8 mmol), as prepared in Example 33, was dissolved in 75 ml of CH$_2$Cl$_2$. The solution was cooled to 0° C. and 37 ml of BBr$_3$ (396 mmol) was added dropwise for 1 h 30 min. The reaction mixture was then stirred at room temperature until complete transformation of the starting material as monitored by HPLC. The reaction mixture was evaporated to dryness. A cold saturated solution of NaHCO$_3$ was added and the resulting solid filtered and dried. This solid was mixed with pyridine hydrochloride salt (46 g, 396 mmol). The mixture was heated to 189° C. for 3.5 hours. Subsequently, the reaction was cooled to room temperature. Methanol was added to dissolve the mixture. The obtained dark solution was poured to a saturated NaHCO$_3$ solution and extracted with ethyl acetate. The combined organic phases were washed with brine and dried over MgSO$_4$ to yield a brownish solid that was purified by chromatography on silica gel (loaded with CH$_2$Cl$_2$ and a slight amount of MeOH, eluted with 2%, 2.5%, 3% of MeOH in CH$_2$Cl$_2$) to provide 5,7-dihydroxy-3-(4-hydroxyphenyl)-4(3H)-quinazolinethione (3.4 g, 60%) as a yellow solid.

$C_{14}H_{10}N_2O_3S$=286 g/mol; HPLC purity =98.2%; ESI-LC/MS (M+H)$^+$=287.; MP: 299-302° C.; $^1$H NMR (CD$_3$OD): δ 8.28 (1H, s), 7.18 (2H, d, J=8.8 Hz), 6.93 (2H, d, J=8.8 Hz), 6.52 (1H, d, J=1.7 Hz), 6.42 (1H, d, J=1.7 Hz).

According to the procedures described in Examples 35-37 or 43-45, the following compounds described in Examples 46 to 64 were prepared, starting from the appropriate ethers.

EXAMPLE 46

5,7-dihydroxy-3-(6-hydroxy-3-pyridinyl)-4(3H)-quinazolinone

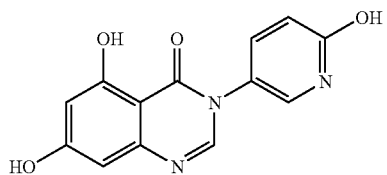

Purified by preparative HPLC and obtained as an off-white solid.

$C_{13}H_9N_3O_4$=271 g/mol; HPLC purity=98%; ESI-LC/MS (M+H)$^+$272.; MP: >360° C.; $^1$H NMR (DMSO-D$_6$): δ 11.6 (1H, s), 10.7 (1H, s) 8.18 (1H, s), 7.77 (1H, d, J=2.6 Hz), 7.59 (1H, q, J=2.6 Hz and J=9.7 Hz), 6.51 (1H, d, J=2.2 Hz), 6.42 (1H, d, J=9.7 Hz) 6.34 (1H, d, J=2.2 Hz).

EXAMPLE 47

5,7-dihydroxy-3-(4-hydroxyphenyl)-2-methyl-4(3H)-quinazolinone

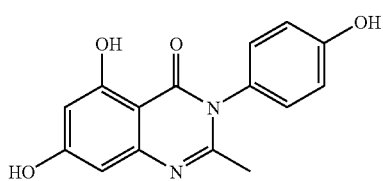

$C_{15}H_{12}N_2O_4$=284.27 g/mol; purity (by NMR)=95%; ESI-LC/MS (M+H)$^+$=285.04; ESI-LC/MS (M−H)$^-$=283.02; $^1$H NMR (CD$_3$OD): δ 2.17 (3H, s), 6.29 (1H, d, J=2.2 Hz), 6.47 (1H, d, J=2.2 Hz), 6.94 (2H, d, J=8.8 Hz), 7.14 (2H, d, J=8.8 Hz).

EXAMPLE 48

5,7-dihydroxy-2-ethyl-3-(4-hydroxyphenyl)-4(3H)-quinazolinone

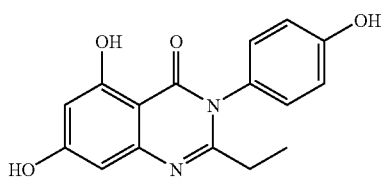

$C_{16}H_{14}N_2O_4$=298.30 g/mol; HPLC purity=95%; ESI-LC/MS (M−H)$^-$=297.17; $^1$H NMR (CD$_3$OD): δ 1.07 (3H, t, J=7.5 Hz), 2.35 (2H, q, J=7.5 Hz), 6.20 (1H, d, J=2.2 Hz), 6.44 (1H, d, J=2.2 Hz), 6.85 (2H, d, J=8.8 Hz), 7.05 (2H, d, J=8.8 Hz).

EXAMPLE 49

5,7-dihydroxy-2-propyl-3-(4-hydroxyphenyl)-4(3H)-quinazolinone

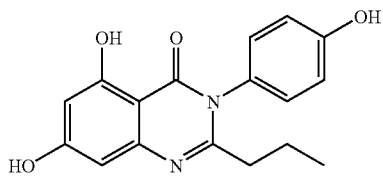

$C_{17}H_{16}N_2O_4$=312. g/mol; HPLC purity=95%; ESI-LC/MS (M+H)$^+$=313.1; ESI-LC/MS (M−H)$^-$=311.0; $^1$H NMR (CD$_3$OD): δ 0.77 (3H, t, J=7.46 Hz), 1.57 (2H, m), 2.37 (2H, t, J=7.7 Hz), 6.24 (1H, d, J=2 Hz), 6.44 (1H, d, J=2 Hz), 6.86 (2H, d, J=8.8 Hz), 7.07 (2H, d, J=8.8 Hz).

EXAMPLE 50

5,7-dihydroxy-2-isopropyl-3-(4-hydroxyphenyl)-4(3H)-quinazolinone

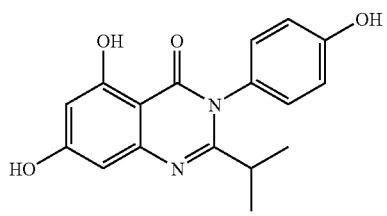

$C_{17}H_{16}N_2O_4$=312.33 g/mol; HPLC purity=96%; ESI-LC/MS (M+H)$^+$=313.0; ESI-LC/MS (M−H)$^-$=311.0; $^1$H NMR (CD$_3$OD): δ 1.08 (6H, d, J=6.6 Hz), 2.61 (1H, m) 6.08 (1H, d, J=2.2 Hz), 6.34 (1H, d, J=2.2 Hz), 6.83 (2H, d, J=8.8 Hz), 7.01 (2H, d, J=8.8 Hz).

EXAMPLE 51

5,7-dihydroxy-2-butyl-3-(4-hydroxyphenyl)-4(3H)-quinazolinone

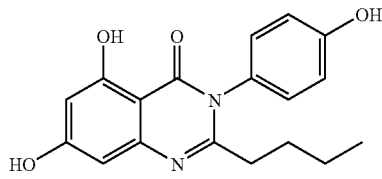

$C_{18}H_{18}N_2O_4$: 326 g/mol; HPLC purity 99%; ESI-LC/MS (M+H)$^+$=327.13; ESI-LC/MS (M−H)$^-$=325.09; $^1$H NMR (CD$_3$OD): δ 0.71 (3H, t, J=7.5 Hz), 1.14 (2H, m), 1.50 (2H, m), 2.32 (2H, t, J=7.9 Hz), 6.19 (1H, d, J=2.2 Hz), 6.41 (1H, d, J=2.2 Hz), 6.85 (2H, d, J=8.6 Hz), 7.05 (2H, d, J=8.6 Hz).

EXAMPLE 52

5,7-dihydroxy-2-isobutyl-3-(4-hydroxyphenyl)-4(3H)-quinazolinone

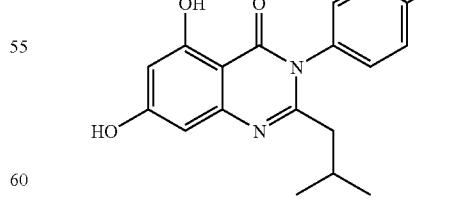

$C_{18}H_{18}N_2O_4$=326 g/mol; HPLC purity=96%; ESI-LC/MS (M+H)$^+$=327.17; ESI-LC/MS (M−H)$^-$=325.12; $^1$H NMR (CD$_3$OD): δ 0.76 (6H, d, J=6.6 Hz), 1.94 (1H, m) 2.24 (2H, d, J=7 Hz), 6.21 (1H, d, J=2.2 Hz), 6.43 (1H, d, J=2.2 Hz), 6.85 (2H, d, J=8.8 Hz), 7.03 (2H, d, J=8.8 Hz).

EXAMPLE 53

5,7-dihydroxy-3-(4-hydroxyphenyl)-2,4(1I3H)-quinazolindione

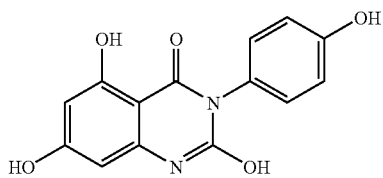

$C_{14}H_{10}N_2O_5$=286 g/mol; HPLC purity=85%; ESI-LC/MS (M+H)⁺=287.02; ESI-LC/MS (M–H)⁻=284.99; ¹H NMR (CD₃OD): δ 5.98 (1H, d, J=2.2 Hz), 6.09 (1H, d, J=2.2 Hz), 6.68 (2H, d, J=8.8 Hz), 7.33 (2H, d, J=8.8 Hz).

EXAMPLE 54

3-(3-chloro-4-hydroxyphenyl)-5,7-dihydroxy-4(3H)-quinazolinone

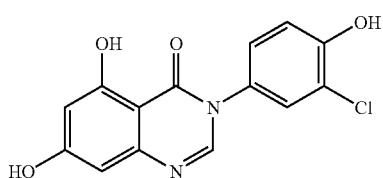

$C_{14}H_9ClN_2O_4$=304 g/mol; HPLC purity=96%; ESI/MS (M+H)⁺=304.8; ¹H NMR (DMSO-d₆): δ 11.7 (1H, s), 10.7 (1H, s), 8.18 (1H, s), 7.62 (1H, d, J=2.2 Hz), 7.30 (1H, d, J=8.8 Hz), 7.08 (1H, d, J=8.8 Hz), 6.52 (1H, d, J=1.8 Hz), 6,34 (1H, d, J=2.2 Hz).

EXAMPLE 55

5,7-dihydroxy-3-(3-fluoro-4-hydroxyphenyl)-4(3H)-quinazolinone

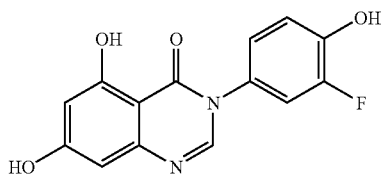

$C_{14}H_9FN_2O_4$=288 g/mol; HPLC purity=97%; ESI-LC/MS (M+H)⁺=288.9; ¹H NMR (DMSO-d₆): δ 11.7 (1H, s), 10.6 (1H, broad), 8.18 (1H, s), 7.47 (1H, dd, J=2.2 Hz and J=11.9 Hz), 7.18 (1H, d, J=8.8 Hz), 7.07 (1H, t, J=9 Hz), 6.52 (1H, d, J=1.8 Hz), 6.34 (1H, d, J=2.2 Hz).

EXAMPLE 56

5,7-dihydroxy-3-(3-fluoro-4-hydroxyphenyl)-4(3H)-quinazolinone

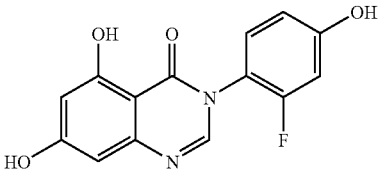

$C_{14}H_9FN_2O_4$=288 g/mol; HPLC purity=99%; ESI-LC/MS (M+H)⁺288.8; ¹H NMR (DMSO-d₆): δ 11.5 (1H, s), 10.6 (1H, broad), 8.19 (1H, s), 7.44 (1H, t, J=8.8 Hz), 6.77 (2H, m), 6.54 (1H, d, J=2.2 Hz), 6.36 (1H, d, J=2.2 Hz).

EXAMPLE 57

3-(3-chloro-4-hydroxyphenyl)-5,7-dihydroxy-4(3H)-quinazolinone

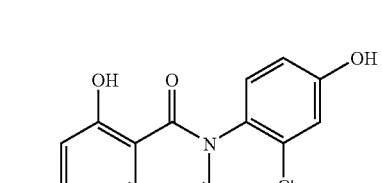

$C_{14}H_9ClN_2O_4$=304 g/mol; HPLC purity=99%; ESI-LC/MS (M+H)⁺=304.8; ¹H NMR (DMSO-d₆): δ 11.5 (1H, s), 10.6 (1H, broad), 8.14 (1H, s), 7.49 (1H, d, J=8.4 Hz), 7.05 (1H, d, J=2.6 Hz), 6.90 (1H, dd, J=2.6 Hz and J=8.4 Hz), 6.55 (1H, d, J=1.8 Hz), 6.36 (1H, d, J=2.2 Hz).

EXAMPLE 58

3-(4-hydroxyphenyl)-5,7-dihydroxy-2-mercapto-4(1,3H)-quinazolinone

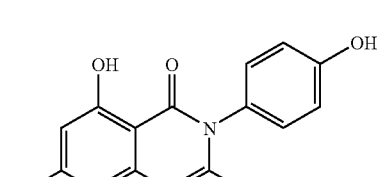

$C_{14}H_{10}N_2O_4S$=302 g/mol; HPLC purity=89% MP=320-326° C.; ESI-LC/MS (M+H)⁺=303; ¹H NMR (400 MHz, CD₃OD): δ 7.01 (2H, d, J=8.8 Hz), 6.86 (2H, d, J=8.8 Hz), 6.16 (1H, d, J=1.9 Hz), 6.11 (1H, d, J=1.9 Hz).

EXAMPLE 59

5,7-dihydroxy-3-(4-hydroxy-2-methylphenyl)-4(3H)-quinazolinone

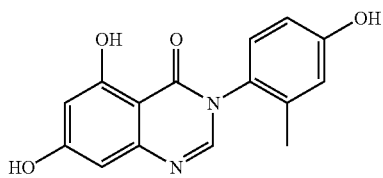

$C_{15}H_{12}N_2O_4$=284 g/mol; HPLC purity=99%; ESI-LC/MS (M+H)$^+$=285.0; $^1$H NMR (DMSO-$d_6$): δ 11.7 (1H, s), 10.7 (1H, s), 9.79 (1H, s), 8.09 (1H, s), 7.20 (1H, d, J=8.4 Hz), 6.78 (1H, d, J=2.2 Hz), 6.72 (1H, dd, J=2.6 Hz and J=8.8 Hz ), 6.53 (1H, d, J=1.8 Hz), 6.34 (1H, d, J=2.2 Hz), 2.01 (3H, s).

EXAMPLE 60

5,7-dihydroxy-3-(5-hydroxy-2-pyridyl)-4(3H)-quinazolinone

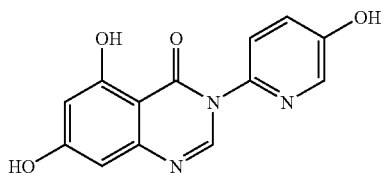

$C_{13}H_9N_3O_4$=271.06 g/mol; HPLC purity 97%; ESI-LC/MS (M+H)$^+$=271.8; ESI-LC/MS (M−H)$^-$=269.8; $^1$H NMR (400 MHz, DMSO-$d_6$): δ 11.64 (1H, s), 10.65 (1H, s), 8.3 (1H, s), 8.13 (1H, d, J=2.6 Hz), 7.59 (1H, d, J=8.4 Hz), 7.4 (1H, q, J=2.6 Hz and 8.4 Hz), 6.56 (1H, d, J=1.8 Hz), 6.36 (1H, d, J=1.8 Hz).

EXAMPLE 61

5,7-dihydroxy-3-(4-hydroxy-3-methylphenyl)-4(3H)-quinazolin thione

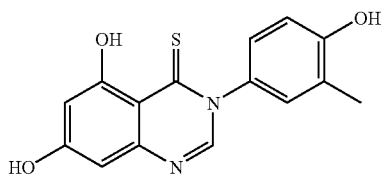

$C_{15}H_{12}N_2O_3S$=300.8 g/mol; HPLC purity=99%; ESI-LC/MS (M+H)$^+$=300.8 ESI-LC/MS (M−H)$^-$=298.8; $^1$H NMR (400 MHz, DMSO-$d_6$): δ 13.52 (1H, s), 11.03 (1H, s), 9.86 (1H, s), 8.34 (1H, s), 7.15 (1H, s), 7.07 (1H, d, J=8.8 Hz), 6.90 (1H, d, J=8.8 Hz), 6.58 (1H, d, J=1.8 Hz), 6.46 (1H, d, J=1.8 Hz), 2.15 (3H, s).

EXAMPLE 62

2-chloro-5,7-dihydroxy-3-(4-hydroxyphenyl)-4(3H)-quinazolinone

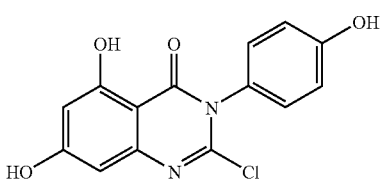

$C_{14}H_9ClN_2O_4$=304.03 g/mol; HPLC purity=99%; ESI-LC/MS (M+H)$^+$=304.9; ESI-LC/MS (M−H)$^-$=302.96; $^1$H NMR (CD$_3$OD): δ 7.16 (2H, m), 6.91 (2H, m), 6.47 (1H, d, J=2.2 Hz), 6.35 (1H, d, J=2.2 Hz).

EXAMPLE 63

5,7-dihydroxy-3-(3-fluoro-4-hydroxyphenyl)-4(3H)-quinazolin thione

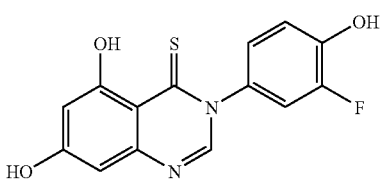

$C_{14}H_9FN_2O_3S$=304.3 g/mol; HPLC purity=99%; ESI-LC/MS (M+H)$^+$=304.9 ESI-LC/MS (M−H)$^-$=302.8; $^1$H NMR (500 MHz, DMSO-$d_6$): δ 13.43 (1H, s), 11.06 (1H, s), 10.43 (1H, s), 8.37 (1H, s), 7.43 (1H, d, J=11.9 Hz), 7.12 (2H, m), 6.58 (1H, d, J=2.3 Hz), 6.46 (1H, d, J=2.3 Hz).

EXAMPLE 64

5,7-dihydroxy-3-(4-hydroxy-3-methylphenyl)-4(3H)-quinazolinone

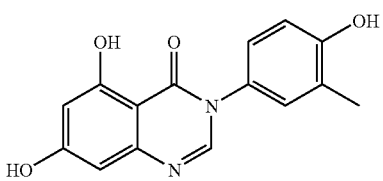

$C_{15}H_{12}N_2O_4$=284.27 g/mol; HPLC purity=99%; ESI-LC/MS (M+H)$^+$=284.8 ESI-LC/MS (M−H)$^-$=282.9; $^1$H NMR (400 MHz, DMSO-$d_6$): δ 11.78 (1H, s), 9.85 (1H, s) 8.15 (1H, s), 7.22 (1H, s), 7.13 (1H, d, J=8.4 Hz), 6.90 (1H, d, J=8.8 Hz), 6.52 (1H, s), 6.34 (1H, s), 2.16 (3H, s).

What is claimed is:

1. A compound of the formula I

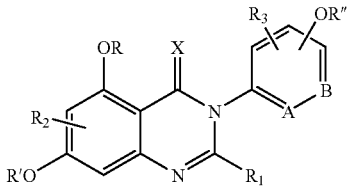

wherein
X is O;
A and B are each independently CR''' or N, wherein A and B are each CR''', or one of A and B is CR''' and the of A and B is N;
R is H;
R' is H;
$R_2$ is H;
R'' is selected from the group consisting of hydrogen, alkyl, benzyl, p-methoxybenzyl, allyl and $Si(R_4)_3$;
R''' is selected from the group consisting of hydrogen, halogen, $CF_3$, $OR_5$, $S(O)_nR_6$, $NR_7R_8$, cycloalkyl and alkyl;
$R_1$ and $R_3$ are each independently selected from the group consisting of hydrogen, halogen, $CF_3$, $OR_5$, $S(O)_nR_6$, $NR_7R_8$, cycloalkyl and alkyl, wherein alkyl is unsubstituted or is substituted with halo, alkyl, alkoxy, aryl, aryloxy, arylalkyl, arylalkyloxy, alkenyl, alkynyl, cycloalkyl, cycloalkenyl, cycloalkylalkyl, cycloalkylalkyloxy, hydroxyl, hydroxyalkyl, acyl, oxo, alkanoyl, arylalkoxycarbonyl, aryloxyalkyl, aryloxyaryl, alkanoylamino, arylcarbonylamino, nitro, cyano, thiol, haloalkyl, trihaloalkyl or alkylthio;
$R_4$ is a alkyl;
$R_5$, $R_6$, $R_7$ and $R_8$ in each functional group are each independently selected from the group consisting of hydrogen, cycloalkyl and alkyl; and
n is an integer from 0 to 2,
and prodrug esters and pharmaceutically acceptable salts thereof;
wherein the term "prodrug esters" refers to esters and carbonates formed by reacting one or more free hydroxyls, that is, where any of R, R' and/or R'' is H, of the compound of formula I with alkyl, alkoxy, or aryl substituted acylating agents.

2. A compound having the structure Ia:

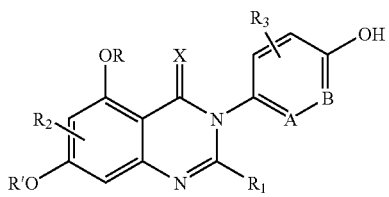

wherein
X is O;
A and B are each independently CR''' or N, wherein A and B are each CR''', or one of A and B is CR''' and the other of A and B is N;

R and R' are each hydrogen;
$R_2$ is hydrogen;
R''' is selected from the group consisting of hydrogen, halogen, $CF_3$, $OR_5$, $S(O)_nR_6$, $NR_7R_8$, cycloalkyl and alkyl;
$R_1$ and $R_3$ are each independently selected from the group consisting of hydrogen, halogen, $CF_3$, $OR_5$, $S(O)_nR_6$, $NR_7R_8$, cycloalkyl and alkyl, wherein alkyl is unsubstituted or is substituted with halo, alkyl, alkoxy, aryl, aryloxy, arylalkyl, arylalkyloxy, alkenyl, alkynyl, cycloalkyl, cycloalkenyl, cycloalkylalkyl, cycloalkylalkyloxy, hydroxyl, hydroxyalkyl, acyl, oxo, alkanoyl, arylalkoxycarbonyl, aryloxyalkyl, aryloxyaryl, alkanoylamino, arylcarbonylamino, nitro, cyano, thiol, haloalkyl, trihaloalkyl or alkylthio;
$R_4$ is a alkyl;
$R_5$, $R_6$, $R_7$ and $R_8$ in each functional group are each independently selected from the group consisting of hydrogen, cycloalkyl and alkyl;
n is an integer from 0 to 2; and
prodrug esters and pharmaceutically acceptable salts thereof,
wherein the term "prodrug esters" refers to esters and carbonates formed by reacting one or more free hydroxyls, of the compound of formula Ia, with alkyl, alkoxy or aryl substituted acylating agents.

3. The compound as defined in claim 2 wherein
R and R' are hydrogen; and
$R_1$, $R_2$, $R_3$ hydrogen.

4. The compound as defined in claim 2 wherein
$R_1$ is hydrogen; and
$R_3$ is fluoro, chloro or methyl.

5. The compound as defined in claim 2 having the structure

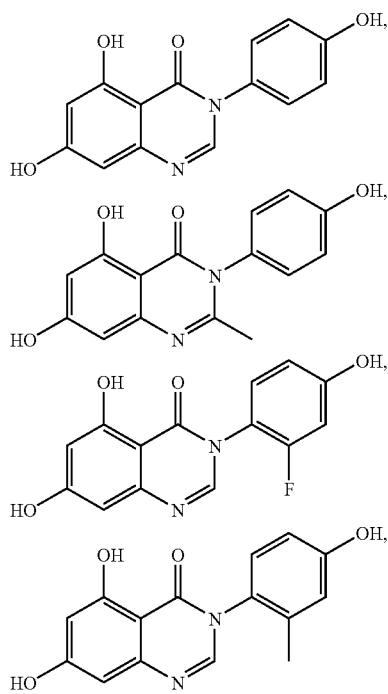

-continued

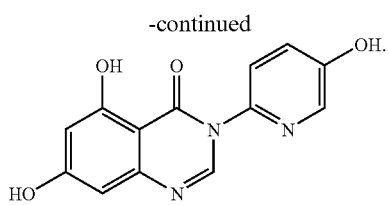

6. A pharmaceutical composition comprising a compound as defined in claim 1 and at least one additional therapeutic agent selected from the group consisting of other compounds of formula I, anti-osteoporosis agents, cholesterol lowering agents, growth promoting agents, modulators of bone resorption which are selected from estrogen, selective estrogen receptor modulators, selective androgen receptor modulators; vitamin D; elemental calcium and calcium supplements; cathepsin_K inhibitors; chloride channel inhibitors; Src $SH_2$ antagonists; Src kinase inhibitors; vacular $H^+$-ATPase inhibitors; osteoprotegrin; Tibolone; prostanoids; PPAR gamma antagonists or isoflavinoids; androgens; RANK ligand antagonists; AP-1 inhibitors and progesterone receptor agonists; and cardiovascular agents.

7. The pharmaceutical composition as defined in claim 6 wherein said cholesterol lowering agent is selected from the group consisting of pravastatin, lovastatin, simvastatin, atorvastatin, fluvastatin and cerivastatin.

8. The pharmaceutical composition as defined in claim 6 wherein said anti-osteoporosis agent is selected from the group consisting of bisphosphonates, parathyroid hormones, PTH fragments which are PTH-(1-84) and PTH-(1-34), and calcitonins.

9. A method for treating osteoporosis, prostatic hypertrophy, endometrial hyperplasia or breast cancer, which comprises administrating to a mammalian species in need of treatment a therapeutically effective amount of a compound as defined in claim 1.

10. The method according to claim 9 further comprising administering, concurrently or sequentially, a therapeutically effective amount of at least one additional therapeutic agent selected from the group consisting of other compounds of formula I, anti-osteoporosis agents, cholesterol lowering agents, growth promoting agents, modulators of bone resorption which are selected from estrogen, selective estrogen receptor modulators, selective androgen receptor modulators; vitamin D; elemental calcium and calcium supplements; cathepsin K inhibitors; chloride channel inhibitors; Src $SH_2$ antagonists; Src kinase inhibitors; vacular $H^+$-ATPase inhibitors; osteoprotegrin; Tibolone; prostanoids; PPAR gamma antagonists or isoflavinoids; androgens; RANK ligand antagonists; AP-1 inhibitors and progesterone receptor agonists; and cardiovascular agents.

11. A method for treating osteoporosis which comprises administering to mammalian patient in need of treatment a therapeutically effective amount of a compound as defined in claim 1.

12. The method according to claim 11 further comprising administering, concurrently or sequentially, a therapeutically effective amount of at least one additional therapeutic agent selected from the group consisting of anti-osteoporosis agents, growth promoting agents and modulators of bone resorption which are selected from estrogen, selective estrogen receptor modulators, estrogen, selective estrogen receptor modulators, selective androgen receptor modulators; vitamin D; elemental calcium and calcium supplements; cathepsin K inhibitors; chloride channel inhibitors; Src $SH_2$ antagonists; Src kinase inhibitors; vacular $H^+$-ATPase inhibitors; osteoprotegrin; Tibolone; prostanoids; PPAR gamma antagonists or isoflavinoids; androgens; RANK ligand antagonists; AP-1 inhibitors and progesterone receptor agonists.

13. A pharmaceutical composition comprising a compound of formula I as defined in claim 1

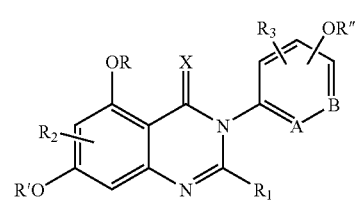

wherein
R is H;
R' is H;
$R_2$ is H;
X is O;
A and B are each independently CR''' or N, wherein A and B are each CR''', or one of A and B is CR''' and the other of A and B is N;
R'' is selected from the group consisting of hydrogen, alkyl, benzyl, p-methoxybenzyl, allyl and $Si(R_4)_3$;
R''' is selected from the group consisting of hydrogen, halogen, $CF_3$, $OR_5$, $S(O)_nR_6$, $NR_7R_8$, cycloalkyl and alkyl;
$R_1$ and $R_3$ are each independently selected from the group consisting of hydrogen, halogen, $CF_3$, $OR_5$, $S(O)_nR_6$, $NR_7R_8$, cycloalkyl and alkyl;
$R_4$ is a alkyl:
$R_5$, $R_6$, $R_7$ and $R_8$ in each functional group are each independently selected from the group consisting of hydrogen, cycloalkyl and alkyl; and
n is an integer from 0 to 2, and
prodrug esters and pharmaceutically acceptable salts thereof;
and a pharmaceutically acceptable carrier; wherein the term "prodrug esters" refers to esters and carbonates formed by reacting one or more free hydroxyls, that is, where any of R, R' and/or R'' is H, of the compound of formula I with alkyl, alkoxy or aryl substituted acylating agents.

14. A compound of the formula I

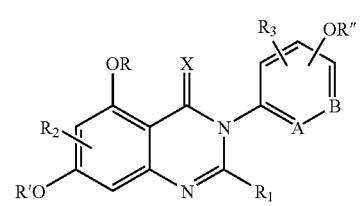

wherein
X is S;
A and B are each independently CR''' or N, wherein A and B are each CR''', or one of A and B is CR''' and the other of A and B is N;

R, R' and R" are each independently selected from the group consisting of hydrogen, alkyl, benzyl, p-methoxybenzyl, allyl and Si(R$_4$)$_3$, wherein at least one of R, R' and R" is hydrogen;

R'" is selected from the group consisting of hydrogen, halogen, CF$_3$, OR$_5$, S(O)$_n$R$_6$, NR$_7$R$_8$, cycloalkyl and alkyl;

R$_1$, R$_2$ and R$_3$ are each independently selected from the group consisting of hydrogen, halogen, CF$_3$, OR$_5$, S(O)$_n$R$_6$, NR$_7$R$_8$, cycloalkyl and alkyl, wherein alkyl is unsubstituted or is substituted with halo, alkyl, alkoxy, aryl, aryloxy, arylalkyl, arylalkyloxy, alkenyl, alkynyl, cycloalkyl, cycloalkenyl, cycloalkylalkyl, cycloalkylalkyloxy, hydroxyl, hydroxyalkyl, acyl, oxo, alkanoyl, arylalkoxycarbonyl, aryloxyalkyl, aryloxyaryl, alkanoylamino, arylcarbonylamino, nitro, cyano, thiol, haloalkyl, trihaloalkyl or alkylthio;

R$_4$ is a alkyl;

R$_5$, R$_6$, R$_7$ and R$_8$ in each functional group are each independently selected from the group consisting of hydrogen, cycloalkyl and alkyl; and n is an integer from 0 to 2, and prodrug esters and pharmaceutically acceptable salts thereof;

wherein the term "prodrug esters" refers to esters and carbonates formed by reacting one or more free hydroxyls, that is, where any of R, R' and/or R" is H, of the compound of formula I with alkyl, alkoxy or aryl substituted acylating agents.

15. A compound having the structure Ia:

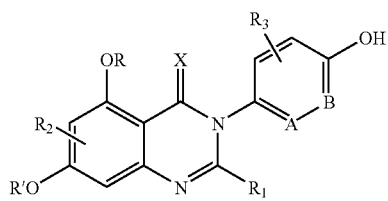

wherein

X is S;

A and B are each independently CR'" or N, wherein A and B are each CR'", or one of A and B is CR'" and the other of A and B is N;

R and R' are each independently selected from the group consisting of hydrogen, alkyl, benzyl, p-methoxybenzyl, allyl and Si(R$_4$)$_3$;

R'" is selected from the group consisting of hydrogen, halogen, CF$_3$, OR$_5$, S(O)$_n$R$_6$, NR$_7$R$_8$, cycloalkyl and alkyl;

R$_1$, R$_2$ and R$_3$ are each independently selected from the group consisting of hydrogen, halogen, CF$_3$, OR$_5$, S(O)$_n$R$_6$, NR$_7$R$_8$, cycloalkyl and alkyl, wherein alkyl is unsubstituted or is substituted with halo, alkyl, alkoxy, aryl, aryloxy, arylalkyl, arylalkyloxy, alkenyl, alkynyl, cycloalkyl, cycloalkenyl, cycloalkylalkyl, cycloalkylalkyloxy, hydroxyl, hydroxyalkyl, acyl, oxo, alkanoyl, arylalkoxycarbonyl, aryloxyalkyl, aryloxyaryl, alkanoylamino, arylcarbonylamino, nitro, cyano, thiol, haloalkyl, trihaloalkyl or alkylthio;

R$_4$ is alkyl;

R$_5$, R$_6$, R$_7$ and R$_8$ in each functional group are each independently selected from the group consisting of hydrogen, cycloalkyl and alkyl;

n is an integer from 0 to 2; and prodrug esters and pharmaceutically acceptable salts thereof, wherein the term "prodrug esters" refers to esters and carbonates formed by reacting one or more free hydroxyls, of the compound of formula Ia, with alkyl, alkoxy or aryl substituted acylating agents.

16. The compound as defined in claim 15 wherein

R and R' are hydrogen; and

R$_1$, R$_2$, R$_3$ are hydrogen.

17. The compound as defined in claim 15 having the structure

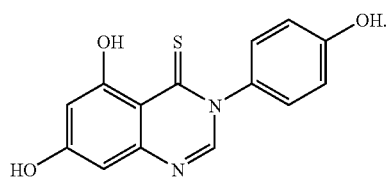

18. A pharmaceutically composition comprising a compound as defined in claim 14 and a pharmaceutically acceptance carrier therefor.

* * * * *

UNITED STATES PATENT AND TRADEMARK OFFICE
CERTIFICATE OF CORRECTION

| | |
|---|---|
| PATENT NO. | : 7,381,730 B2 |
| APPLICATION NO. | : 10/387666 |
| DATED | : June 3, 2008 |
| INVENTOR(S) | : Timur Gungor and James R. Corte |

It is certified that error appears in the above-identified patent and that said Letters Patent is hereby corrected as shown below:

At Column 47, line 18, please insert the word --other-- as indicated below:

B are each CR''' or one of A and B is CR''' and the --other-- of

At Column 48, line 32, please insert the word --are-- as indicated below:

$R_1$, $R_2$, $R_3$ --are-- hydrogen.

At Column 52, lines 45-47, please correct the spelling of "pharmaceutically" to pharmaceutical and please correct the spelling of "acceptance" to acceptable. Thus, Claim 18 should read as follows:

18. A pharmaceutical composition comprising a compound as defined in claim 14 and a pharmaceutically acceptable carrier thereof.

Signed and Sealed this

Seventh Day of April, 2009

JOHN DOLL
*Acting Director of the United States Patent and Trademark Office*